United States Patent
Lawler et al.

(10) Patent No.: US 12,180,155 B2
(45) Date of Patent: *Dec. 31, 2024

(54) CRYSTALLINE FORMS OF A CANNABINOID RECEPTOR TYPE 1 (CB1) MODULATOR AND METHODS OF USE AND PREPARATION THEREOF

(71) Applicant: Anebulo Pharmaceuticals, Inc., Lakeway, TX (US)

(72) Inventors: Joseph Fenton Lawler, Lakeway, TX (US); Daniel Pawel Schneeberger, Austin, TX (US)

(73) Assignee: Anebulo Pharmaceuticals, Inc., Lakeway, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/471,170

(22) Filed: Sep. 20, 2023

(65) Prior Publication Data

US 2024/0010617 A1    Jan. 11, 2024

Related U.S. Application Data

(63) Continuation of application No. 18/045,435, filed on Oct. 10, 2022, now Pat. No. 11,795,146.

(60) Provisional application No. 63/254,417, filed on Oct. 11, 2021.

(51) Int. Cl.
C07D 205/04        (2006.01)

(52) U.S. Cl.
CPC ........ *C07D 205/04* (2013.01); *C07B 2200/13* (2013.01)

(58) Field of Classification Search
CPC .......................... C07D 205/04; C07B 2200/13
See application file for complete search history.

(56) References Cited

U.S. PATENT DOCUMENTS

| | | | |
|---|---|---|---|
| 6,403,574 B1 | 6/2002 | Adams et al. | |
| 6,566,356 B2 | 5/2003 | Achard et al. | |
| 7,232,486 B2 * | 6/2007 | Keri .................... | C07D 498/22 117/70 |
| 7,402,686 B2 * | 7/2008 | Duchek ................ | C07D 311/80 549/390 |
| 7,504,522 B2 * | 3/2009 | Davidson ............. | C07D 405/12 548/953 |
| 8,450,346 B2 | 5/2013 | Roughley et al. | |
| 8,835,418 B2 | 9/2014 | Bartsch et al. | |
| 10,570,146 B2 | 2/2020 | Makriyannis et al. | |
| 11,141,404 B1 | 10/2021 | Lawler et al. | |
| 11,795,146 B2 * | 10/2023 | Lawler .................. | C07D 205/04 |
| 2005/0043327 A1 | 2/2005 | Coe et al. | |
| 2006/0276452 A1 | 12/2006 | Davidson et al. | |
| 2007/0054891 A1 | 3/2007 | Davidson et al. | |
| 2007/0173486 A1 | 7/2007 | Davidson et al. | |
| 2009/0181939 A1 | 7/2009 | Davidson et al. | |
| 2012/0115849 A1 | 5/2012 | Demopulos et al. | |
| 2016/0145294 A1 | 5/2016 | Piazza et al. | |
| 2020/0179271 A1 | 6/2020 | Skolnick | |
| 2020/0181086 A1 | 6/2020 | Jones et al. | |
| 2020/0397749 A1 | 12/2020 | Skolnick | |
| 2022/0033393 A1 | 2/2022 | Makriyannis et al. | |
| 2022/0151990 A1 | 5/2022 | Lawler et al. | |
| 2023/0139815 A1 | 5/2023 | Lawler et al. | |
| 2024/0010617 A1 | 1/2024 | Lawler et al. | |

FOREIGN PATENT DOCUMENTS

| | | |
|---|---|---|
| WO | WO-0107023 A2 | 2/2001 |
| WO | WO-2004096763 A1 | 11/2004 |
| WO | WO-2008024408 A2 | 2/2008 |
| WO | WO-2016201271 A1 | 12/2016 |
| WO | WO-2018204689 A1 | 11/2018 |
| WO | WO-2020051707 A1 | 3/2020 |
| WO | WO-2020118048 A1 | 6/2020 |
| WO | WO-2022109043 A1 | 5/2022 |
| WO | WO-2023064225 A1 | 4/2023 |
| WO | WO-2023064228 A1 | 4/2023 |
| WO | WO-2024073367 A1 | 4/2024 |

OTHER PUBLICATIONS

Klumpers et al., Prediction of a Therapeutically Active Dose of the CB1 Antagonist ANEB-001 For Reversal of Acute Cannabinoid Intoxication Using a PK/PD Model. ACEP, Oct. 9-12, 2023.
Monte et al., Randomized controlled trial of ANEB-001 as an antidote for acute cannabinoid intoxication in health adults. Centre for Human Drug Research, Sep. 29, 2023.
Co-pending U.S. Appl. No. 18/253,025, inventors Lawler; Joseph Fenton et al., filed on May 15, 2023.
FDA Briefing Document. NDA 21-888. Zimulti (rimonabant) Tablets, 20 mg. Sanofi Aventis. Advisory Committee, pp. 1-91 (2007) URL: http://online.wsj.com/public/resources/documents/fdaacomplia20070611.pdf [retrieved online Apr. 9, 2021].
Fong et al.: Pharmacological efficacy and safety profile of taranabant in preclinical species. Drug Development Research 70:349-362 (2009).
Huestis et al.: Single and multiple doses of rimonabant antagonize acute effects of smoked cannabis in male cannabis users. Psychopharmacology (Berl) 194(4):505-515. doi:10.1007/s00213-007-0861-5 (2007).
Ismaili et al.: The Oral Cannabis Poisoning of the Children. Chemical Sciences Journal. 5:1 (2014).
Jones, End of the line for cannabinoid receptor 1 as an anti-obesity target? Nature Reviews 7: 961-962 (2008).
Kelly et al.: Cannabinoid Toxicity. StatPearls Publishing, LLC.
Koch, Taranabant no longer developed as an antiobesity agent. Nature Reviews 6: 300 (2010).

(Continued)

*Primary Examiner* — D Margaret M Seaman
(74) *Attorney, Agent, or Firm* — WILSON SONSINI GOODRICH & ROSATI

(57) ABSTRACT

Described herein are polymorphic forms of a CB1 modulator, methods of making such forms, pharmaceutical compositions and medicaments comprising such forms, and methods of using such forms in the treatment of conditions, diseases, or disorders that would benefit from modulation of the CB1 receptor.

18 Claims, 5 Drawing Sheets

(56) References Cited

OTHER PUBLICATIONS

Lee et al.: Cannabinoid Pharmacokinetic After Controlled Smoking and Ad libitum Cannabis Smoking in Chronic Frequent Users. Journal of Analytical Toxicology. 39:580-587 (2015).

Myers, Merck Discontinues Development of Investigational Medicine Taranabant for Obesity. Fierce Biotech 4 pages (2008).

Nathan et al.: Neuropsychiatric Adverse Effects of Centrally Acting Antiobesity Drugs. CNS Neurosci. Ther. 17:490-505 (2011).

P. Skolnick (lead investigator): Development of Drinabant for Treatment of Acute Cannabinoid Overdose. National Institutes of Health BrIDGs Project, 1 page. Published online URL: https://ncats.nih.gov/bridgs/projects/active/drinabant-acute-cannabinoid-overdose [retrieved online Apr. 9, 2021] Nov. 2, 2020.

PCT/US2021/059747 International Search Report and Written Opinion dated Mar. 8, 2022.

PCT/US2022/046197 International Search Report and Written Opinion dated Jan. 20, 2023.

PCT/US2022/046201 International Search Report and Written Opinion dated Jan. 9, 2023.

Prodrugs : Challenges and Rewards Part 1. Ed Stella et al. Springer Science & Business Media (pp. 160-171) (2007).

Turpault et al.: Rimonabant pharmacokinetics in healthy and obese subjects. Am. Soc. for Clin. Pharm. and Ther. (2005) 79:P50-P50, published Feb. 28, 2006.

U.S. Appl. No. 17/484,593 Non-Final Office Action dated Dec. 9, 2022.

U.S. Appl. No. 18/045,435 Non-Final Office Action dated Mar. 20, 2023.

U.S. Appl. No. 17/100,157 Office Action dated Jan. 28, 2021.

U.S. Appl. No. 17/100,157 Office Action dated May 5, 2021.

U.S. Appl. No. 17/484,593 Final Office Action dated Sep. 19, 2023.

Zuurman et al.: Inhibition of THC-induced effects of the central nervous system and heart rate by a novel CB1 receptor antagonist AVE1625. J. Psychopharm., 24:363 (2010).

Addy et al., Safety, tolerability, pharmacokinetics, and pharmacodynamic properties of taranabant, a novel selective cannabinoid-1 receptor inverse agonist, for the treatment of obesity: results from a double-blind, placebo-controlled, single oral dose study in healthy volunteers. J ournal of Clinical Pharmacology 48:418-427 (2008).

Amato et al., Blocking alcoholic steatosis in mice with a peripherally restricted purine antagonist of the type 1 cannabinoid receptor. J. Med. Chem 61:4370-4385 (2018).

Bundgard, Hans., Design of Prodrugs. Elsevier, Amsterdam: 1-30 (1985).

CAS Registry No. 791847-89-7.

ClinicalTrials.gov. Safety, Tolerability, Pharmacokinetics, and Pharmacodynamics of CB1 Antagonist ANEB-001 in a THC Challenge Test. ClinicalTrials.gov Identifier: NCT05282797. First Posted Mar. 16, 2022.

Co-pending U.S. Appl. No. 18/700,232, inventors Schneeberger; Daniel Pawel et al., filed on Apr. 10, 2024.

Higuchi, T, et al. Pro-Drugs as Novel Delivery Systems, vol. 14 of the A.C.S. Symposium Series. American Chemical Society (1975).

Isele, U et al. Large-scale production of liposomes containing monomeric zinc phthalocyanine by controlled dilution of organic solvents. Journal of pharmaceutical sciences vol. 83,11 (1994): 1608-16. doi:10.1002/jps.2600831117.

Kulkarni, Jayesh A et al. Scalable Production of Lipid Nanoparticles Containing Amphotericin B. Langmuir : the ACS journal of surfaces and colloids vol. 37,24 (2021): 7312-7319. doi:10.1021/acs.langmuir.1c00530.

PCT/US2023/075053 International Search Report and Written Opinion dated Feb. 28, 2024.

Roche, Edward B. Bioreversible Carriers In Drug Design: Theory And Application. American Pharmaceutical Association and Pergamon Press:1-4 (1987).

U.S. Appl. No. 17/484,593 Office Action dated Apr. 25, 2024.

EP21895521.9 Extended European Search Report dated Sep. 24, 2024.

* cited by examiner

CRYSTALLINE FORMS OF A CANNABINOID RECEPTOR TYPE 1 (CB1) MODULATOR AND METHODS OF USE AND PREPARATION THEREOF

CROSS-REFERENCE TO RELATED APPLICATIONS

This application is a continuation of U.S. Non-Provisional application Ser. No. 18/045,435, filed Oct. 10, 2022, which claims the benefit of U.S. Provisional Application No. 63/254,417 filed Oct. 11, 2021, each of which is incorporated herein by reference for all purposes in its entirety.

BACKGROUND

The widespread use of Δ9-tetrahydrocannabinol (THC) and synthetic cannabinoids (SCs) has resulted in an increased number of emergency room visits secondary to symptoms of cannabinoid overdose; this is especially notable after cannabis is legalized in a jurisdiction. A medical need therefore exists to treat THC and SC related-overdoses.

SUMMARY OF THE INVENTION

In a first aspect, the present disclosure provides Crystalline (R)—N-(tert-butyl)-3-((4-chlorophenyl)(2-(trifluoromethyl)phenyl)methoxy)azetidine-1-carboxamide (Compound 1):

Compound 1

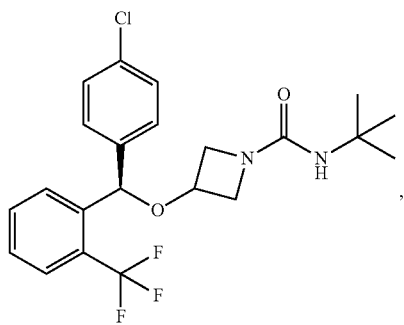

or a pharmaceutically acceptable solvate or hydrate thereof. In some embodiments, the crystals of Crystalline (R)—N-(tert-butyl)-3-((4-chlorophenyl)(2-(trifluoromethyl)phenyl) methoxy)azetidine-1-carboxamide (compound 1) have unit cell parameters at T=160° K of: a=19.371(2) Å, b=9.7283(9) Å, c=25.173(5) Å; β=111.07(1)°, and a chiral monoclinic I2 space group. In some embodiments, the crystalline form is Crystalline Form I. In some embodiments, Crystalline Form I is characterized by:
  (a) an X-ray powder diffraction pattern comprising peaks at 10.2±0.2° 2-θ, 18.1±0.2°2-θ, and 20.7±0.2° 2-θ, as measured by X-ray powder diffraction using an X-ray wavelength of 1.5406 Å;
  (b) an X-ray powder diffraction pattern substantially the same as shown in FIG. 1;
  (c) a differential scanning calorimetry (DSC) thermogram comprising an endotherm in the range of about 80-90° C.;
  (d) a differential scanning calorimetry (DSC) thermogram comprising an endotherm with an onset of about 84° C. and a peak of about 86° C.;
  (e) a differential scanning calorimetry (DSC) thermogram substantially the same as shown in FIG. 2;
  (f) a thermogravimetric analysis (TGA) thermogram substantially the same as shown in FIG. 3;
  (g) a dynamic vapor sorption (DVS) trace substantially the same as shown in FIG. 4;
  (h) a substantially unchanged XPRD after storage at 25° C. and 90% relative humidity (RH);
  (i) a substantially unchanged XPRD after storage at laboratory conditions for at least 5 weeks; or
  (j) combinations thereof.

In some embodiments, the crystalline form is characterized by an X-ray powder diffraction pattern comprising peaks at 10.2±0.2° 2-θ, 18.1±0.2° 2-θ, and 20.7±0.2° 2-θ, and as measured by X-ray powder diffraction using an X-ray wavelength of 1.5406 Å. In some embodiments, the X-ray powder diffraction pattern further comprises at least one peak selected from 9.8±0.2° 2-θ, 15.0±0.2° 2-θ, and 22.9±0.2° 2-θ, as measured by X-ray powder diffraction using an X-ray wavelength of 1.5406 Å. In some embodiments, the X-ray powder diffraction pattern further comprises at least five peaks selected from 7.1±0.2° 2-θ, 11.6±0.2° 2-θ, 13.5±0.2° 2-θ, 14.4±0.2° 2-θ, 14.6±0.2° 2-θ, 14.8±0.2° 2-θ, 16.2±0.2° 2-θ, 19.0±0.2° 2-θ, 19.3±0.2° 2-θ, 19.6±0.2° 2-θ, 20.4±0.2° 2-θ, 22.6±0.2° 2-θ, 23.2±0.2° 2-θ, and 27.7±0.2° 2-θ, as measured by X-ray powder diffraction using an X-ray wavelength of 1.5406 Å. In some embodiments, the X-ray powder diffraction pattern comprises peaks at 7.1±0.2° 2-θ, 9.8±0.2° 2-θ, 10.2±0.2° 2-θ, 11.6±0.2° 2-θ, 13.5±0.2° 2-θ, 14.4±0.2° 2-θ, 14.6±0.2° 2-θ, 14.8±0.2° 2-θ, 15.0±0.2° 2-θ, 16.2±0.2° 2-θ, 18.1±0.2° 2-θ, 19.0±0.2° 2-θ, 19.3±0.2° 2-θ, 19.6±0.2° 2-θ, 20.4±0.2° 2-θ, 20.7±0.2° 2-θ, 22.6±0.2° 2-θ, 22.9±0.2° 2-θ, 23.2±0.2° 2-θ, and 27.7±0.2° 2-θ. In some embodiments, Crystalline Form I is characterized by an X-ray powder diffraction pattern substantially the same as shown in FIG. 1. In some embodiments, Crystalline Form I is characterized by a differential scanning calorimetry (DSC) thermogram comprising an endotherm in the range of about 80-90° C. In some embodiments, Crystalline Form I is characterized by a differential scanning calorimetry (DSC) thermogram comprising an endotherm with an onset of about 84° C. and a peak of about 86° C. In some embodiments, Crystalline Form I is characterized by a differential scanning calorimetry (DSC) thermogram substantially the same as shown in FIG. 2. In some embodiments, Crystalline Form I is characterized by a thermogravimetric analysis (TGA) thermogram substantially the same as shown in FIG. 3. In some embodiments, Crystalline Form I is characterized by a dynamic vapor sorption (DVS) trace substantially the same as shown in FIG. 4. In some embodiments, the crystalline form is Crystalline Form II. In some embodiments, Crystalline Form II is characterized by:
  (a) an X-ray powder diffraction pattern comprising peaks at 15.2±0.2° 2-θ, 18.2±0.2°2-θ, and 20.8±0.2° 2-θ as measured by X-ray powder diffraction using an X-ray wavelength of 1.5406 Å;
  (b) an X-ray powder diffraction pattern substantially the same as shown in FIG. 5;
  (c) a differential scanning calorimetry (DSC) thermogram comprising an endotherm in the range of about 80-90° C.;
  (d) a differential scanning calorimetry (DSC) thermogram comprising an endotherm with an onset of about 81° C. and a peak of about 85° C.;
  (e) a differential scanning calorimetry (DSC) thermogram substantially the same as shown in FIG. 6;

(f) a thermogravimetric analysis (TGA) thermogram substantially the same as shown in FIG. 7;

(g) a dynamic vapor sorption (DVS) trace substantially the same as shown in FIG. 8;

(h) an unchanged XPRD after storage at 25° C. and 90% relative humidity (RH);

(i) an unchanged XPRD after storage at laboratory conditions for at least 5 weeks;

or (j) combinations thereof.

In some embodiments, Crystalline Form II is characterized by an X-ray powder diffraction pattern comprising peaks at 15.2±0.2° 2-θ, 18.2±0.2° 2-θ, and 20.8±0.2° 2-θ, as measured by X-ray powder diffraction using an X-ray wavelength of 1.5406 Å. In some embodiments, the X-ray powder diffraction pattern further comprises at least one peak selected from 10.2±0.2° 2-θ, 19.2±0.2° 2-θ, 20.6±0.2° 2-θ, and 22.8±0.2° 2-θ, as measured by X-ray powder diffraction using an X-ray wavelength of 1.5406 Å. In some embodiments, the X-ray powder diffraction pattern comprises at least five peaks selected from 7.0±0.2° 2-θ, 9.8±0.2° 2-θ, 13.6±0.2° 2-θ, 14.6±0.2° 2-θ, 15.0±0.2° 2-θ, 16.1±0.2° 2-θ, 19.7±0.2° 2-θ, 20.3±0.2° 2-θ, and 20.4±0.2° 2-θ, as measured by X-ray powder diffraction using an X-ray wavelength of 1.5406 Å. In some embodiments, the X-ray powder diffraction pattern comprises peaks at 7.0±0.2° 2-θ, 9.8±0.2° 2-θ, 10.2±0.2° 2-θ, 13.6±0.2° 2-θ, 14.6±0.2° 2-θ, 15.0±0.2° 2-θ, 15.2±0.2° 2-θ, 16.1±0.2° 2-θ, 18.2±0.2° 2-θ, 19.2±0.2° 2-θ, 19.7±0.2° 2-θ, 20.3±0.2° 2-θ, 20.4±0.2° 2-θ, 20.6±0.2° 2-θ, 20.8±0.2° 2-θ, and 22.8±0.2° 2-θ, as measured by X-ray powder diffraction using an X-ray wavelength of 1.5406 Å. In some embodiments, Crystalline Form II is characterized by an X-ray powder diffraction pattern substantially the same as shown in FIG. 5. In some embodiments, Crystalline Form II is characterized by a differential scanning calorimetry (DSC) thermogram comprising an endotherm in the range of about 80-90° C. In some embodiments, Crystalline Form II is characterized by a differential scanning calorimetry (DSC) thermogram comprising an endotherm with an onset of about 81° C. and a peak of about 85° C. In some embodiments, Crystalline Form II is characterized by a differential scanning calorimetry (DSC) thermogram substantially the same as shown in FIG. 6. In some embodiments, Crystalline Form II is characterized by a thermogravimetric analysis (TGA) thermogram substantially the same as shown in FIG. 7. In some embodiments, Crystalline Form II is characterized by a dynamic vapor sorption (DVS) trace substantially the same as shown in FIG. 8.

In a second aspect, the present disclosure provides a pharmaceutical composition comprising crystalline R)—N-(tert-butyl)-3-((4-chlorophenyl)(2-(trifluoromethyl)phenyl)methoxy)azetidine-1-carboxamide, and at least one pharmaceutically acceptable excipient. In some embodiments, the pharmaceutical composition is formulated for oral, parenteral, intravenous (IV), intramuscular (IM), subcutaneous (SC), endotracheal, sublingual, buccal, intralingual, submental, transdermal, suppository, or intranasal administration. In some embodiments, the pharmaceutical composition is formulated for oral administration. In some embodiments, the pharmaceutical composition is in the form of a solid form pharmaceutical composition. In some embodiments, the pharmaceutical composition is formulated in a tablet form. In some embodiments of the pharmaceutical composition, crystalline (R)—N-(tert-butyl)-3-((4-chlorophenyl)(2-(trifluoromethyl)phenyl)methoxy)azetidine-1-carboxamide is subjected to spray drying prior to being formulated.

In a third aspect, the present disclosure provides a method of treating known or suspected acute drug overdose reaction in a subject in need thereof, comprising administering to the subject a therapeutically effective amount of crystalline (R)—N-(tert-butyl)-3-((4-chlorophenyl)(2-(trifluoromethyl)phenyl)methoxy)azetidine-1-carboxamide or a pharmaceutical composition described herein. In some embodiments of the method, the subject shows signs of an acute cannabinoid overdose. In some embodiments, the acute cannabinoid overdose is caused by a compound from the *Cannabis* genus. In some embodiments, the acute cannabinoid overdose is caused by a synthetic cannabinoid. In some embodiments, the acute cannabinoid overdose is caused by oral ingestion of cannabinoids or synthetic cannabinoids. In some embodiments, the synthetic cannabinoid is capable of binding to the Cannabinoid 1 (CB1) receptor. In some embodiments, the subject shows signs of cannabinoid hyperemesis syndrome. In some embodiments, the method further comprises treatment for drug overdose prior to treatment with crystalline (R)—N-(tert-butyl)-3-((4-chlorophenyl)(2-(trifluoromethyl)phenyl)methoxy)azetidine-1-carboxamide. In some embodiments, the prior treatment comprises one or more of administration of an opiate antagonist, activated charcoal or emetic. In some embodiments, the method further comprises a diagnostic test prior to treatment with crystalline (R)—N-(tert-butyl)-3-((4-chlorophenyl)(2-(trifluoromethyl)phenyl)methoxy)azetidine-1-carboxamide. In some embodiments, the diagnostic test is a blood test. In some embodiments, the subject has a cannabinoid plasma concentration of at least 50 μg/L. In some embodiments, the subject has a cannabinoid plasma concentration of 50 μg/L to 300 μg/L. In some embodiments of the method, the amount of crystalline (R)—N-(tert-butyl)-3-((4-chlorophenyl)(2-(trifluoromethyl)phenyl)methoxy)azetidine-1-carboxamide is 1 mg to 200 mg. In some embodiments, the amount of crystalline (R)—N-(tert-butyl)-3-((4-chlorophenyl)(2-(trifluoromethyl)phenyl)methoxy) azetidine-1-carboxamide is 25 mg to 200 mg. In some embodiments, the amount of crystalline (R)—N-(tert-butyl)-3-((4-chlorophenyl)(2-(trifluoromethyl)phenyl)methoxy) azetidine-1-carboxamide is 50 mg to 200 mg. In some embodiments of the method, the pharmaceutical composition is formulated to deliver a therapeutically effective amount of crystalline (R)—N-(tert-butyl)-3-((4-chlorophenyl)(2-(trifluoromethyl)phenyl)methoxy)azetidine-1-carboxamide in no more than 10 minutes. In some embodiments, the pharmaceutical composition is formulated to deliver a therapeutically effective amount of the crystalline (R)—N-(tert-butyl)-3-((4-chlorophenyl)(2-(trifluoromethyl)phenyl)methoxy)azetidine-1-carboxamide in no more than 5 minutes. In some embodiments of the method, the amount of (R)—N-(tert-butyl)-3-((4-chlorophenyl)(2-(trifluoromethyl)phenyl)methoxy)azetidine-1-carboxamide in the bloodstream of the subject reaches at least 200 ng/mL within one hour after oral administration. In some embodiments, the amount of (R)—N-(tert-butyl)-3-((4-chlorophenyl)(2-(trifluoromethyl)phenyl)methoxy)azetidine-1-carboxamide in the bloodstream of the subject reaches at least 200 ng/mL within one hour after oral administration. In some embodiments, the amount of (R)—N-(tert-butyl)-3-((4-chlorophenyl)(2-(trifluoromethyl)phenyl)methoxy)azetidine-1-carboxamide in the bloodstream of the subject reaches at least 200 ng/mL within 30 minutes after oral administration. In some embodiments, the method is capable of ameliorating one or more symptoms of the acute drug overdose reaction in no more than 30 minutes. In some embodiments, the method is capable of ameliorating one or more symptoms of the acute drug overdose reaction in no more than 1 hour. In some embodiments of the method, the crystalline (R)—N-(tert-butyl)-3-((4-chlorophenyl)(2-(trifluoromethyl)phenyl)methoxy)azetidine-1-carboxamide is Crystalline Form I. In some embodiments of the method, the crystalline (R)—N-(tert-butyl)-3-((4-chlorophenyl)(2-(trifluoromethyl)phenyl)methoxy)azetidine-1-carboxamide is Crystalline Form II.

In a fourth aspect, the present disclosure provides a method of using crystalline (R)—N-(tert-butyl)-3-((4-chlorophenyl)(2-(trifluoromethyl)phenyl)methoxy)azetidine-1-carboxamide, or the pharmaceutical composition described herein as pre-exposure prophylactic therapy, comprising administering a therapeutically effective amount of crystalline (R)—N-(tert-butyl)-3-((4-chlorophenyl)(2-(trifluoromethyl)phenyl)methoxy)azetidine-1-carboxamide prior to exposure to a cannabinoid. In some embodiments, the cannabinoid is tetrahydrocannabinol (THC). In some embodiments, the amount of crystalline (R)—N-(tert-butyl)-3-((4-chlorophenyl)(2-(trifluoromethyl)phenyl)methoxy)azetidine-1-carboxamide is 1 mg to 200 mg. In some embodiments, the amount of crystalline (R)—N-(tert-butyl)-3-((4-chlorophenyl)(2-(trifluoromethyl)phenyl)methoxy)azetidine-1-carboxamide is 25 mg to 200 mg. In some embodiments, the amount of crystalline (R)—N-(tert-butyl)-3-((4-chlorophenyl)(2-(trifluoromethyl)phenyl)methoxy)azetidine-1-carboxamide is 50 mg to 200 mg. In some embodiments, the crystalline (R)—N-(tert-butyl)-3-((4-chlorophenyl)(2-(trifluoromethyl)phenyl)methoxy)azetidine-1-carboxamide is Crystalline Form I. In some embodiments, the crystalline (R)—N-(tert-butyl)-3-((4-chlorophenyl)(2-(trifluoromethyl)phenyl)methoxy)azetidine-1-carboxamide is Crystalline Form II. In some embodiments, the amount of (R)—N-(tert-butyl)-3-((4-chlorophenyl)(2-(trifluoromethyl)phenyl)methoxy)azetidine-1-carboxamide in the bloodstream of the subject reaches at least 200 ng/mL within one hour after oral administration. In some embodiments, the amount of (R)—N-(tert-butyl)-3-((4-chlorophenyl)(2-(trifluoromethyl)phenyl)methoxy)azetidine-1-carboxamide in the bloodstream of the subject reaches at least 200 ng/mL within 30 minutes after oral administration.

In another aspect, the present disclosure provides a method of treating a subject suspected of a drug overdose, comprising administering a therapeutically effective amount of crystalline (R)—N-(tert-butyl)-3-((4-chlorophenyl)(2-(trifluoromethyl)phenyl)methoxy)azetidine-1-carboxamide to the subject and monitoring the subject for reduced symptoms associated with overdose. In some embodiments, the monitoring comprises monitoring heart rate or respiration. In some embodiments, the amount of crystalline (R)—N-(tert-butyl)-3-((4-chlorophenyl)(2-(trifluoromethyl)phenyl)methoxy)azetidine-1-carboxamide is 1 mg to 200 mg. In some embodiments, the crystalline (R)—N-(tert-butyl)-3-((4-chlorophenyl)(2-(trifluoromethyl)phenyl)methoxy)azetidine-1-carboxamide is Crystalline Form I. In some embodiments, the crystalline (R)—N-(tert-butyl)-3-((4-chlorophenyl)(2-(trifluoromethyl)phenyl)methoxy)azetidine-1-carboxamide is Crystalline Form II.

In yet another aspect, the present disclosure provides a method of treating cannabis use disorder (CUD) in a subject in need thereof, comprising administering a therapeutically effective amount of crystalline (R)—N-(tert-butyl)-3-((4-chlorophenyl)(2-(trifluoromethyl)phenyl)methoxy)azetidine-1-carboxamide, or the pharmaceutical composition described herein. In some embodiments, the subject is addicted to a compound from the *Cannabis* genus. In some embodiments, the subject is addicted to a synthetic cannabinoid. In some embodiments, the synthetic cannabinoid is capable of binding to the CB1 receptor. In some embodiments, the subject has a cannabinoid plasma concentration of at least 50 μg/L. In some embodiments, the amount of the crystalline (R)—N-(tert-butyl)-3-((4-chlorophenyl)(2-(trifluoromethyl)phenyl)methoxy)azetidine-1-carboxamide is 1 mg to 200 mg. In some embodiments, the pharmaceutical composition is formulated to deliver a therapeutically effective amount of crystalline (R)—N-(tert-butyl)-3-((4-chlorophenyl)(2-(trifluoromethyl)phenyl)methoxy)azetidine-1-carboxamide in no more than 10 minutes or 5 minutes. In some embodiments, the amount of crystalline (R)—N-(tert-butyl)-3-((4-chlorophenyl)(2-(trifluoromethyl)phenyl)methoxy)azetidine-1-carboxamide in the bloodstream of the subject reaches at least 200 ng/mL within one hour or 30 minutes after oral administration. In some embodiments, the method is capable of ameliorating one or more symptoms of the acute drug overdose reaction in no more than 30 minutes or 1 hour. In some embodiments, the method reduces the subject's ability to experience euphoria after inhaling or consuming *Cannabis* or a synthetic cannabinoid. In some embodiments, the method promotes cessation of cannabis addition and/or consumption in the subject. In some embodiments of the method, the crystalline (R)—N-(tert-butyl)-3-((4-chlorophenyl)(2-(trifluoromethyl)phenyl)methoxy)azetidine-1-carboxamide is Crystalline Form I. In some embodiments of the method, the crystalline (R)—N-(tert-butyl)-3-((4-chlorophenyl)(2-(trifluoromethyl)phenyl)methoxy)azetidine-1-carboxamide is Crystalline Form II.

In yet another aspect, the present disclosure provides an injectable composition for treating a suspected drug overdose in a subject, the composition comprising crystalline (R)—N-(tert-butyl)-3-((4-chlorophenyl)(2-(trifluoromethyl)phenyl)methoxy)azetidine-1-carboxamide, or the pharmaceutical composition described herein, an opioid antagonist, and a benzodiazepine antagonist. In some embodiments, the benzodiazepine antagonist is flumazenil. In some embodiments, the opioid antagonist is naloxone. In some embodiments, the injectable composition is formulated in a single dose injectable device.

In one aspect, the present disclosure provides a method of preparing Crystalline Form I of (R)—N-(tert-butyl)-3-((4-chlorophenyl)(2-(trifluoromethyl)phenyl)methoxy)azetidine-1-carboxamide, wherein the method comprises:
  (a) dissolving the (R)—N-(tert-butyl)-3-((4-chlorophenyl)(2-(trifluoromethyl)phenyl)methoxy)azetidine-1-carboxamide in a solvent to obtain a solution; and
  (b) crystallizing the solution obtained in step (a) to obtain Crystalline Form I of (R)—N-(tert-butyl)-3-((4-chlorophenyl)(2-(trifluoromethyl)phenyl)methoxy)azetidine-1-carboxamide.

In some embodiments of the method of preparing, the solvent in step (a) comprises water, heptane, methanol, acetone, or a combination thereof. In some embodiments, the solvent in step (a) is heptane. In some embodiments, the solve in step (a) is a mixture of acetone and water. In some embodiments, the concentration of the solution obtained in step (a) is between about 20 mg/mL to about 300 mg/mL. In some embodiments, the concentration of the solution obtained in step (a) is between about 40 mg/mL to about 250 mg/mL. In some embodiments, the concentration of the solution obtained in step (a) is between about 100 mg/mL to about 200 mg/mL. In some embodiments, the concentration of the solution obtained in step (a) is between about 125 mg/mL to about 175 mg/mL.

In one aspect provided herein are crystalline forms of (R)—N-(tert-butyl)-3-((4-chlorophenyl)(2-(trifluoromethyl)

phenyl)methoxy)azetidine-1-carboxamide (Compound 1) that are stable at room temperature or about 20° C. In some embodiments the compound is stable for at least six months. In some embodiments the compound is stable for at least 12 months. In some embodiments the compound is stable for at least 24 months. In some embodiments the compound is stable under a relative humidity of at least 90%. In some embodiments the compound is stable under a relative humidity of at least 50%.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

DESCRIPTION OF THE DRAWINGS

The novel features of the present disclosure are set forth with particularity in the appended claims. An understanding of the features and advantages of the present disclosure may be obtained by reference to the following detailed description that sets forth illustrative embodiments, in which the principles of the present disclosure are utilized, and the accompanying drawings of which:

DETAILED DESCRIPTION OF THE INVENTION

Figure 1:
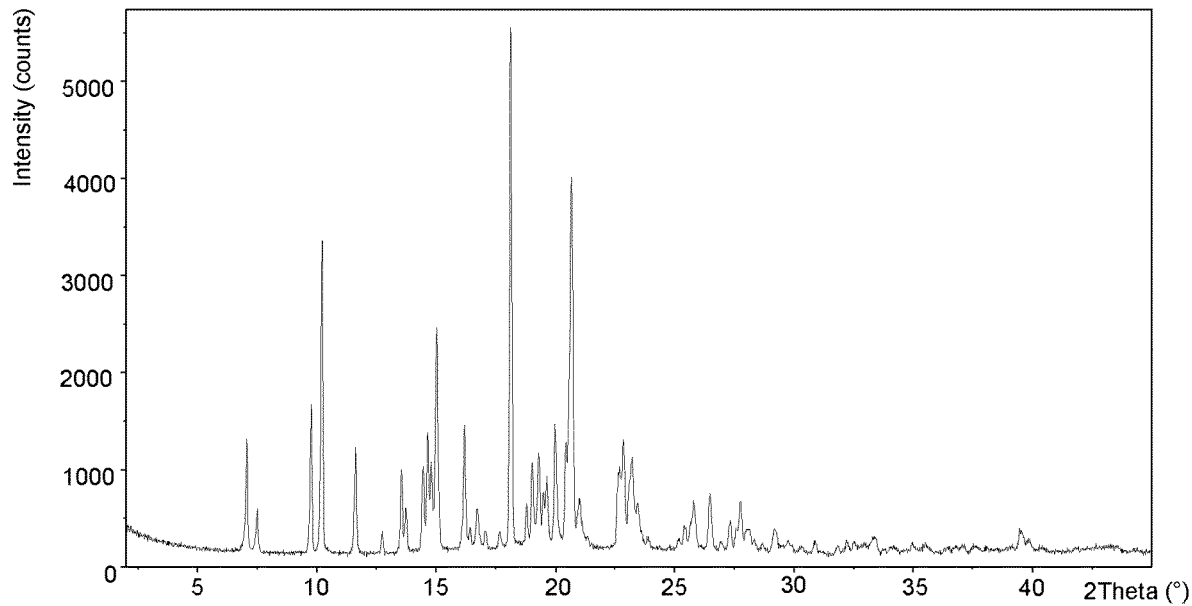
FIG. 1 shows the X-ray powder diffraction (XRPD) pattern for Crystalline Form I of Compound 1. The y-axis is labeled Intensity (counts) from 0-5000 at 1000 unit intervals; the x-axis is labeled 2Theta(°) from 0-40 at 5 unit intervals.

Polymorphic forms of a small molecule drug candidate, such as a Cannabinoid Receptor Type 1 (CB1) modulator, can have different physical properties, including melting point, apparent solubility, dissolution rate, optical and mechanical properties, vapor pressure, and density. These properties can have a direct effect on the ability to process or manufacture a drug substance and the drug product. Moreover, differences in these properties can and often lead to different pharmacokinetics profiles for different polymorphic forms of a drug. Polymorphism can affect the quality, safety, and/or efficacy of a drug product, such as a CB1 modulator. Thus, there still remains a need for polymorphs of CB1 modulators. The present disclosure addresses this need and provides related advantages as well.

Compound 1

As described herein, Compound 1 refers to (R)—N-(tert-butyl)-3-((4-chlorophenyl)(2-(trifluoromethyl)phenyl) methoxy)azetidine-1-carboxamide, which has the chemical structure as shown below:

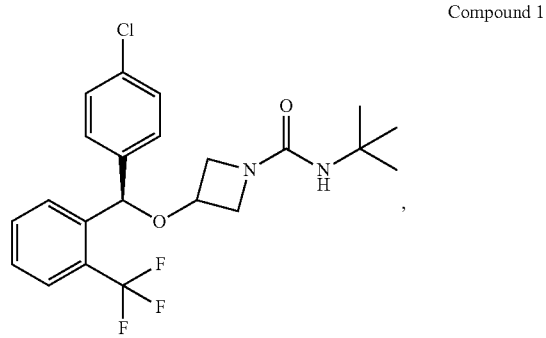 [SMILES: CC(C)(C)NC(=O)N1CC(O[C@H](c2ccc(Cl)cc2)c2ccccc2C(F)(F)F)C1]

Compound 1 or a pharmaceutically acceptable solvate or hydrate thereof.

Compound 1 is a CB1 modulator. CB1 modulators, such as a CB1 inhibitor, are useful in the treatment of various conditions and disorders, including but not limited to acute drug and cannabis overdose and cannabis use disorder.

The preparation and uses of Compound 1 have been previously described (see, Example 81 of U.S. Pat. No. 7,504,522, which is incorporated by reference).

In some embodiments as disclosed herein, Compound 1 is crystalline.

As used herein, "crystalline form," "polymorph," "Form," and "form" may be used interchangeably herein, and are meant to include all crystalline and amorphous forms of the compound, including, for example, polymorphs, pseudopolymorphs, salts, solvates, hydrates, unsolvated polymorphs (including anhydrates), conformational polymorphs, and amorphous forms, as well as mixtures thereof, unless a particular crystalline or amorphous form is referred to. Compounds of the present disclosure include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. In some embodiments, the crystalline form is a single solid state form, e.g., crystalline Form I.

Crystalline Forms of Compound 1

In a first aspect, the present disclosure provides Crystalline (R)—N-(tert-butyl)-3-((4-chlorophenyl)(2-(trifluoromethyl)phenyl)methoxy)azetidine-1-carboxamide (Compound 1):

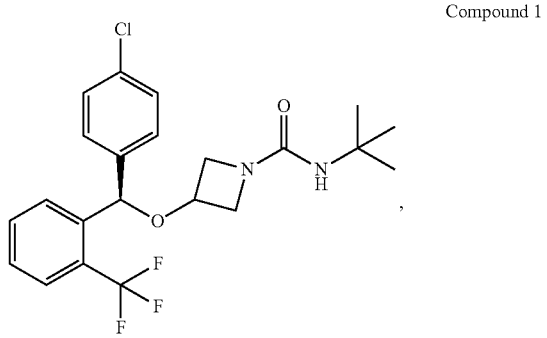 [SMILES: CC(C)(C)NC(=O)N1CC(O[C@H](c2ccc(Cl)cc2)c2ccccc2C(F)(F)F)C1]

Compound 1 or a pharmaceutically acceptable solvate or hydrate thereof.

In some embodiments, the crystals of Crystalline (R)—N-(tert-butyl)-3-((4-chlorophenyl)(2-(trifluoromethyl)phenyl)methoxy)azetidine-1-carboxamide (compound 1) have unit cell parameters at T=160° K of: a=19.371(2) A, b=9.7283(9) A, c=25.173(5) Å; β=111.07(1)°, and a chiral monoclinic 12 space group.

The polymorphs made according to the methods of the present disclosure may be characterized by any methodology according to the art. For example, the polymorphs made according to the methods of the present disclosure may be characterized by X-ray powder diffraction (XRPD), differential scanning calorimetry (DSC), thermogravimetric analysis (TGA), and/or spectroscopy (e.g., Raman, solid state nuclear magnetic resonance (ssNMR), and infrared (IR)). In some embodiments, crystallinity of solid form is determined by X-Ray Powder Diffraction (XPRD).

XRPD: Polymorphs according to the present disclosure may be characterized by XRPD. The relative intensities of XRPD peaks can vary, depending upon the particle size, the sample preparation technique, the sample mounting procedure and the particular instrument employed. Moreover, instrument variation and other factors can affect the 2-θ values. Therefore, the XRPD peak assignments can vary, for example by plus or minus about 0.2 degrees.

Figure 2:
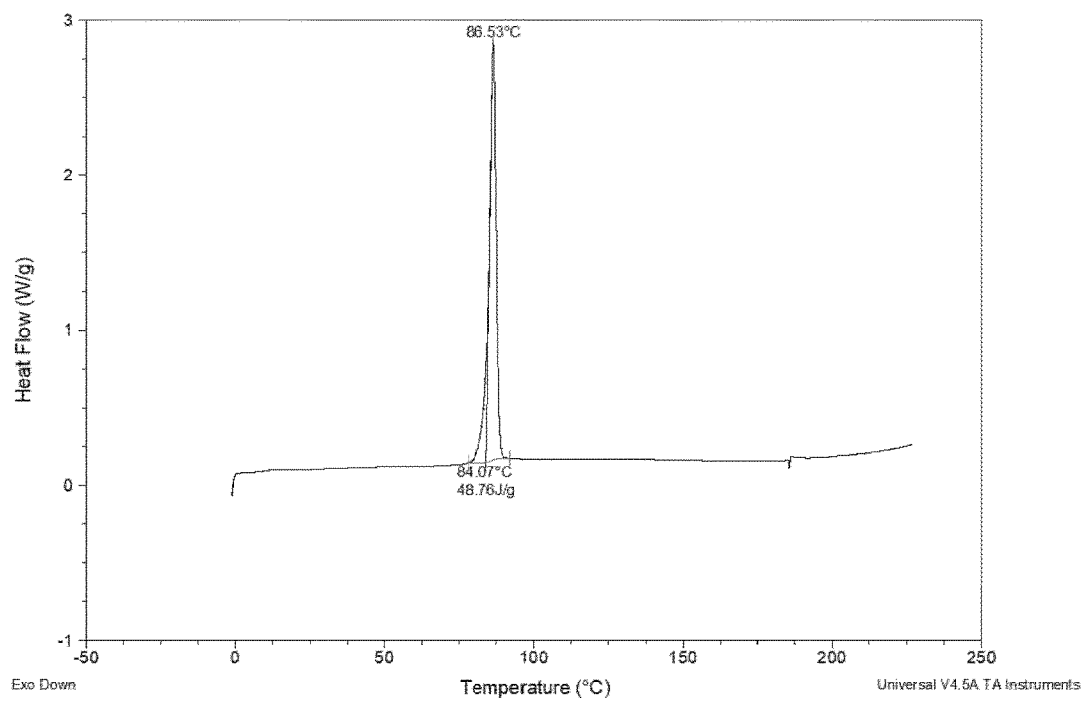
FIG. 2 shows the differential scanning calorimetry (DSC) thermogram for Crystalline Form I of Compound 1. The y-axis is labeled Heat Flow (W/g) from −1 to 3 at 1 unit intervals; the x-axis is labeled Temperature (degrees Celsius) from −50 to 250 at 50 unit intervals. The top of the peak 86.53 degrees Celsius, and the area at the bottom of the peak is labeled 84.07 degrees Celsius 48.76 J/g.
Figure 5:
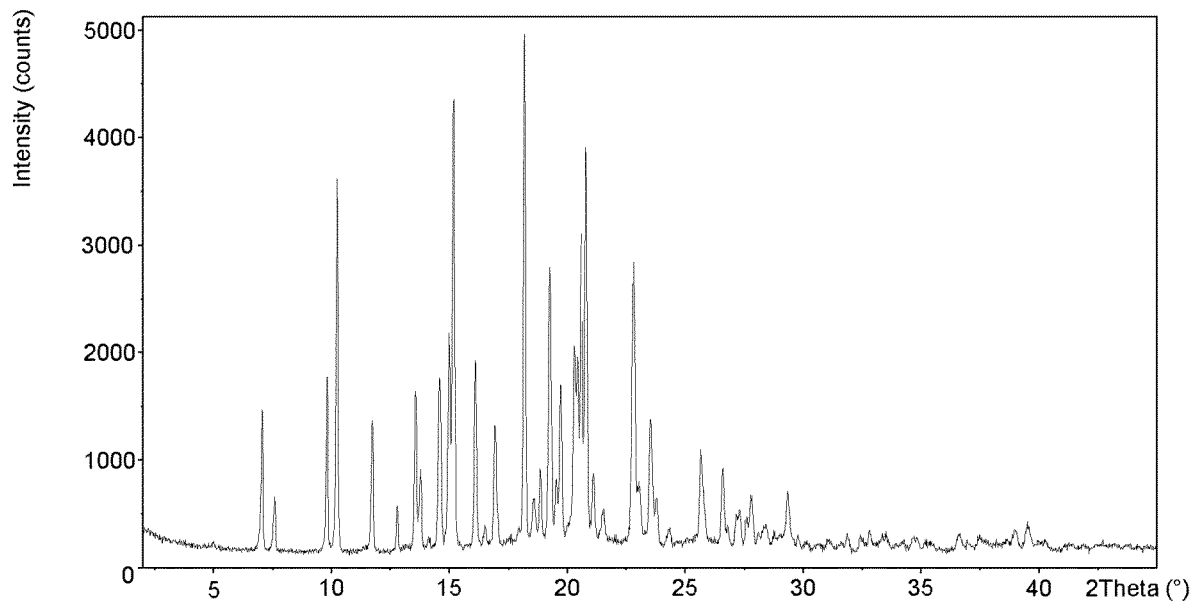
FIG. 5 shows the X-ray powder diffraction (XRPD) pattern for Crystalline Form II of Compound 1. The y-axis is labeled Intensity (counts) from 0-5000 at 1000 unit intervals; the x-axis is labeled 2Theta(°) from 0-40 at 5 unit intervals.

DSC: Polymorphs according to the present disclosure can also be identified by its characteristic DSC thermograms such as shown in FIGS. 2, 5 etc. For DSC, it is known that the temperatures observed will depend upon the rate of temperature change as well as sample preparation technique and the particular instrument employed. Thus, the values reported herein relating to DSC thermograms can vary, for example by plus or minus about 4° C.

TGA: Polymorphs according to the present disclosure may also give rise to thermal behavior different from that of the amorphous material or another polymorphic form. Thermal behavior may be measured in the laboratory by thermogravimetric analysis (TGA) which may be used to distinguish some polymorphic forms from others. In one aspect, the polymorphs as described herein may be characterized by thermogravimetric analysis.

DVS: Polymorphs according to the present disclosure may also give rise to vapors sorption behavior different from that of the amorphous material or another polymorphic form. The vapor sorption behavior may be measured in the laboratory by dynamic vapor sorption (DVS) which may be used to distinguish some polymorphic forms from others. In one aspect, the polymorphs as described herein may be characterized by dynamic vapor sorption.

The polymorph forms of Compound 1 are useful in the production of medicinal preparations and can be obtained by means of a crystallization process to produce crystalline and semi-crystalline forms or a solidification process to obtain the amorphous form. In various embodiments, the crystallization is carried out by either generating the desired compound (for example Compound 1) in a reaction mixture and isolating the desired polymorph from the reaction mixture, or by dissolving raw compound in a solvent, optionally with heat, followed by crystallizing/solidifying the product by cooling (including active cooling) and/or by the addition of an antisolvent for a period of time. The crystallization or solidification may be followed by drying carried out under controlled conditions until the desired water content is reached in the end polymorphic form.

In some embodiments, the various polymorph Forms disclosed herein (e.g., Crystalline Form I and Crystalline Form II of Compound 1) are stable at room temperature. In some examples, the various polymorphs can be stored at room temperature for an extended period of time without significant chemical degradation or change in the crystalline form. In some examples, the various polymorphs can be stored at room temperature for a time period of at least about 10 days, 30 days, 60 days, 90 days, 120 days, 150 days, or 180 days. In some examples, the various polymorphs can be stored at room temperature for a time period of more than about 180 days. In some examples, the various polymorphs can be stored at room temperature for a time period of 10-14 days, 10-18 days, 10-22 days, 10-26 days, 10-30 days, 10-40 days, 10-50 days, 10-60 days, 10-90 days, 10-120 days, 10-150 days, 10-180 days, 14-18 days, 14-22 days, 14-26 days, 14-30 days, 14-40 days, 14-50 days, 14-60 days, 14-90 days, 14-120 days, 14-150 days, 14-180 days, 18-22 days, 18-26 days, 18-30 days, 18-40 days, 18-50 days, 18-60 days, 18-90 days, 18-120 days, 18-150 days, 18-180 days, 22-26 days, 22-30 days, 22-40 days, 22-50 days, 22-60 days, 22-90 days, 22-120 days, 22-150 days, 22-180 days, 26-30 days, 26-40 days, 26-50 days, 26-60 days, 26-90 days, 26-120 days, 26-150 days, 26-180 days, 30-40 days, 30-50 days, 30-60 days, 30-90 days, 30-120 days, 30-150 days, 30-180 days, 40-50 days, 40-60 days, 40-90 days, 40-120 days, 40-150 days, 40-180 days, 50-60 days, 50-90 days, 50-120 days, 50-150 days, 50-180 days, 60-90 days, 60-120 days, 60-150 days, 60-180 days, 90-120 days, 90-150 days, or 90-180 days. In some examples, the various polymorphs can be stored at room temperature for a time period of at least 10 days, 14 days, 18 days, 22 days, 26 days, 30 days, 40 days, 50 days, 60 days, 90 days, 120 days, 150 days, or 180 days. In some instances, various polymorphs are stored for these periods of time under relative humidity conditions, such as at least 10, 20, 30, 40, 50, 60, 70, 80, 90, or at least 100% humidity. In some instances, stable storage results in the polymorphs remaining substantially unchanged.

Crystalline Form I of Compound 1

FIG. 1 shows the X-ray powder diffraction (XPRD) pattern for Crystalline Form I of Compound 1.

FIG. 2 shows the differential scanning calorimetry (DSC) thermogram for Crystalline Form I of Compound 1.

Figure 3:
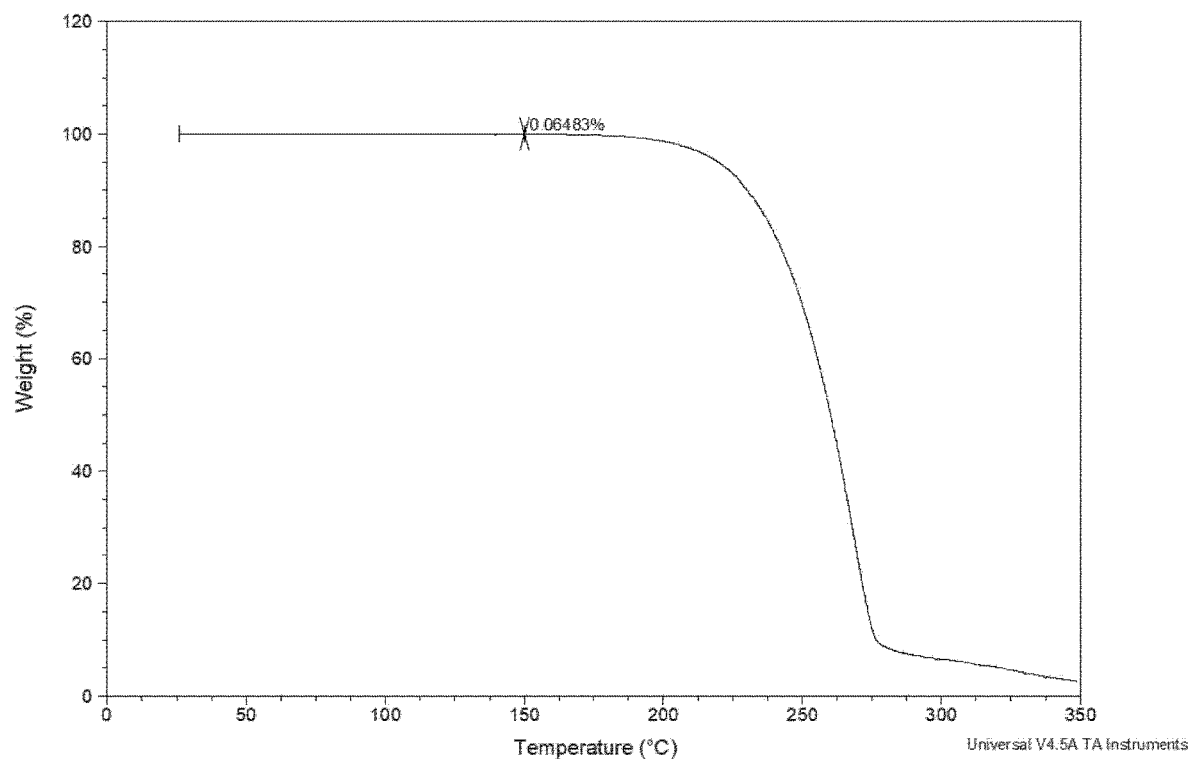
FIG. 3 shows the thermogravimetric analysis (TGA) thermogram for Crystalline Form I of Compound 1. The y-axis is labeled weight (%) from 0-120 at 20 unit intervals; the x-axis is labeled Temperature (degrees Celsius) from 0-350 at 50 unit intervals. Labeled with an X on the trace is 0.06483%.

FIG. 3 shows the thermogravimetric analysis (TGA) thermogram for Crystalline Form I of Compound 1.

Figure 4:
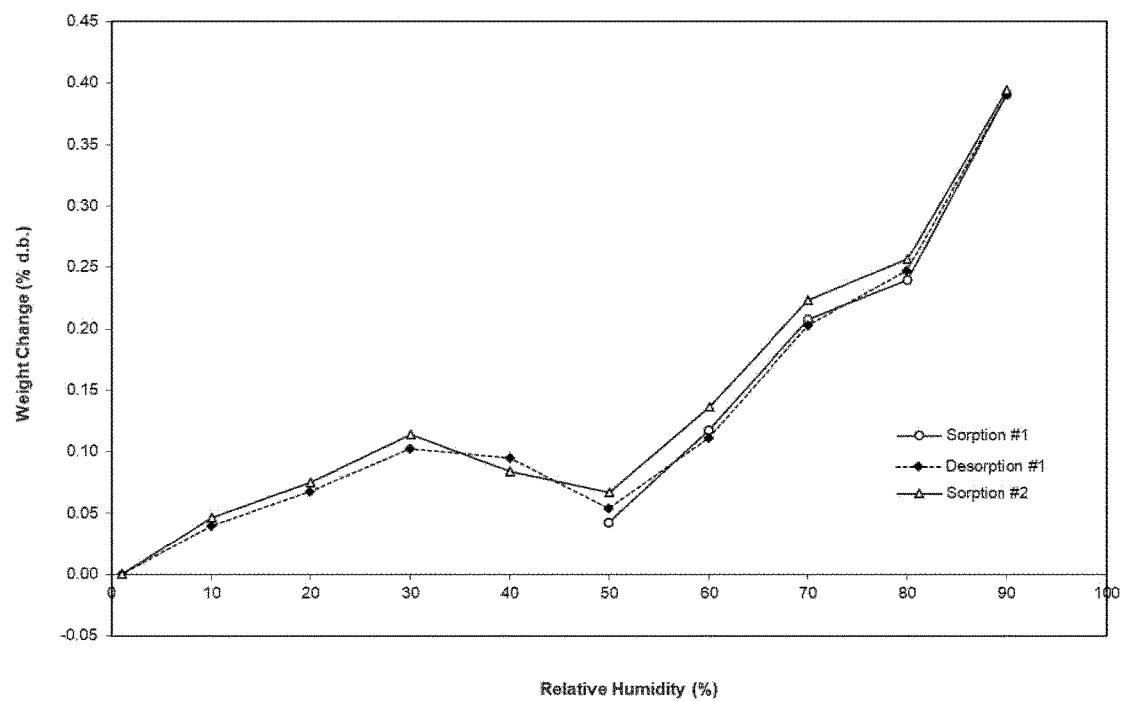
FIG. 4 shows the dynamic vapor sorption (DVS) trace for Crystalline Form I of Compound 1. The y-axis is labeled weight change (% d.b.) from −0.05 to 0.45 at 0.05 unit intervals; the x-axis is labeled relative humidity (%) from 0 to 100 at 10 unit intervals. The legend depicts Sorption #1 (solid line, open circles); Desorption #1 (dotted line, filled diamonds); and Sorption #2 (solid line, open triangles).

FIG. 4 shows the dynamic vapor sorption (DVS) trace for Crystalline Form I of Compound 1.

In some embodiments, the crystalline form of compound 1 is Crystalline Form I. In some embodiments, Crystalline Form I is characterized by:
(a) an X-ray powder diffraction pattern comprising peaks at 10.2±0.2° 2-θ, 18.1±0.2°2-θ, and 20.7±0.2° 2-θ, as measured by X-ray powder diffraction using an X-ray wavelength of 1.5406 Å;
(b) an X-ray powder diffraction pattern substantially the same as shown in FIG. 1;
(c) a differential scanning calorimetry (DSC) thermogram comprising an endotherm in the range of about 80-90° C.;
(d) a differential scanning calorimetry (DSC) thermogram comprising an endotherm with an onset of about 84° C. and a peak of about 86° C.;
(e) a differential scanning calorimetry (DSC) thermogram substantially the same as shown in FIG. 2;
(f) a thermogravimetric analysis (TGA) thermogram substantially the same as shown in FIG. 3;
(g) a dynamic vapor sorption (DVS) trace substantially the same as shown in FIG. 4;
(h) an unchanged XPRD after storage at 25° C. and 90% relative humidity (RH);
(i) an unchanged XPRD after storage at laboratory conditions for at least 5 weeks;
or
(j) combinations thereof.

Compound 1

In some embodiments, the crystalline form of compound 1 is Crystalline Form I. In some embodiments, Crystalline Form I is characterized by:
(a) an X-ray powder diffraction pattern comprising peaks at 10.2±0.2° 2-θ, 18.1±0.2°2-θ, and 20.7±0.2° 2-θ, as measured by X-ray powder diffraction using an X-ray wavelength of 1.5406 Å;
(b) an X-ray powder diffraction pattern substantially the same as shown in FIG. 1;
(c) a differential scanning calorimetry (DSC) thermogram comprising an endotherm in the range of about 80-90° C.;
(d) a differential scanning calorimetry (DSC) thermogram comprising an endotherm with an onset of about 84° C. and a peak of about 86° C.;
(e) a differential scanning calorimetry (DSC) thermogram substantially the same as shown in FIG. 2;
(f) a thermogravimetric analysis (TGA) thermogram substantially the same as shown in FIG. 3;
(g) a dynamic vapor sorption (DVS) trace substantially the same as shown in FIG. 4;
(h) a substantially unchanged XPRD after storage at 25° C. and 90% relative humidity (RH);
(i) a substantially unchanged XPRD after storage at laboratory conditions for at least 5 weeks;
or
(j) combinations thereof.

In some embodiments, Crystalline Form I is characterized by an X-ray powder diffraction pattern substantially the same as shown in FIG. 1.

In some embodiments, the crystalline form is characterized by an X-ray powder diffraction pattern comprising peaks at 10.2±0.2° 2-θ, 18.1±0.2° 2-θ, and 20.7±0.2° 2-θ, and as measured by X-ray powder diffraction using an X-ray wavelength of 1.5406 Å. In some embodiments, Crystalline Form I is characterized by an X-ray powder diffraction pattern comprising peaks at about 10.2° 2-θ, about 18.1° 2-θ, and about 20.7° 2-θ, as measured by X-ray powder diffraction using an X-ray wavelength of 1.5406 Å.

In some embodiments, the X-ray powder diffraction pattern further comprises at least one peak selected from 9.8±0.2° 2-θ, 15.0±0.2° 2-θ, and 22.9±0.2° 2-θ, as measured by X-ray powder diffraction using an X-ray wavelength of 1.5406 Å. In some embodiments, the X-ray powder diffraction pattern further comprises at least one peak selected from about 9.8° 2-θ, about 15.0° 2-θ, and about 22.9° 2-θ, as measured by X-ray powder diffraction using an X-ray wavelength of 1.5406 Å.

In some embodiments, the X-ray powder diffraction pattern further comprises at least one peak selected from 7.1±0.2° 2-θ, 11.6±0.2° 2-θ, 13.5±0.2° 2-θ, 14.4±0.2° 2-θ, 14.6±0.2° 2-θ, 14.8±0.2° 2-θ, 16.2±0.2° 2-θ, 19.0±0.2° 2-θ, 19.3±0.2° 2-θ, 19.6±0.2° 2-θ, 20.4±0.2°2-θ, 22.6±0.2° 2-θ, 23.2±0.2° 2-θ, and 27.7±0.2° 2-θ, as measured by X-ray powder diffraction using an X-ray wavelength of 1.5406 Å. In some embodiments, the X-ray powder diffraction pattern further comprises at least one peak selected from about 7.1° 2-θ, about 11.6°2-θ, about 13.5° 2-θ, about 14.4° 2-θ, about 14.6° 2-θ, about 14.8° 2-θ, about 16.2° 2-θ, about 19.0° 2-θ, about 19.3° 2-θ, about 19.6° 2-θ, about 20.4° 2-θ, about 22.6° 2-θ, about 23.2° 2-θ, and about 27.7° 2-θ, as measured by X-ray powder diffraction using an X-ray wavelength of 1.5406 Å.

In some embodiments, the X-ray powder diffraction pattern comprises peaks at 7.1±0.2° 2-θ, 9.8±0.2° 2-θ, 10.2±0.2° 2-θ, 11.6±0.2° 2-θ, 13.5±0.2° 2-θ, 14.4±0.2° 2-θ, 14.6±0.2° 2-θ, 14.8±0.2° 2-θ, 15.0±0.2° 2-θ, 16.2±0.2° 2-θ, 18.1±0.2° 2-θ, 19.0±0.2° 2-θ, 19.3±0.2° 2-θ, 19.6±0.2° 2-θ, 20.4±0.2° 2-θ, 20.7±0.2° 2-θ, 22.6±0.2° 2-θ, 22.9±0.2° 2-θ, 23.2±0.2° 2-θ, and 27.7±0.2° 2-θ, as measured by X-ray powder diffraction using an X-ray wavelength of 1.5406 Å. In some embodiments, the X-ray powder diffraction pattern comprises at least one peak selected from 7.1±0.2° 2-θ, 9.8±0.2° 2-θ, 10.2±0.2° 2-θ, 11.6±0.2° 2-θ, 13.5±0.2° 2-θ, 14.4±0.2° 2-θ, 14.6±0.2° 2-θ, 14.8±0.2° 2-θ, 15.0±0.2° 2-θ, 16.2±0.2° 2-θ, 18.1±0.2° 2-θ, 19.0±0.2° 2-θ, 19.3±0.2° 2-θ, 19.6±0.2° 2-θ, 20.4±0.2° 2-θ, 20.7±0.2° 2-θ, 22.6±0.2° 2-θ, 22.9±0.2° 2-θ, 23.2±0.2° 2-θ, and 27.7±0.2° 2-θ, as measured by X-ray powder diffraction using an X-ray wavelength of 1.5406 Å. In some embodiments, the X-ray powder diffraction pattern comprises at least two peaks selected from 7.1±0.2° 2-θ, 9.8±0.2° 2-θ, 10.2±0.2° 2-θ, 11.6±0.2° 2-θ, 13.5±0.2° 2-θ, 14.4±0.2° 2-θ, 14.6±0.2° 2-θ, 14.8±0.2° 2-θ, 15.0±0.2° 2-θ, 16.2±0.2° 2-θ, 18.1±0.2° 2-θ, 19.0±0.2°

2-θ, 19.3±0.2° 2-θ, 19.6±0.2° 2-θ, 20.4±0.2° 2-θ, 20.7±0.2° 2-θ, 22.6±0.2° 2-θ, 22.9±0.2° 2-θ, 23.2±0.2° 2-θ, and 27.7±0.2° 2-θ, as measured by X-ray powder diffraction using an X-ray wavelength of 1.5406 Å. In some embodiments, the X-ray powder diffraction pattern comprises at least three peaks selected from 7.1±0.2° 2-θ, 9.8±0.2° 2-θ, 10.2±0.2° 2-θ, 11.6±0.2° 2-θ, 13.5±0.2° 2-θ, 14.4±0.2° 2-θ, 14.6±0.2° 2-θ, 14.8±0.2° 2-θ, 15.0±0.2° 2-θ, 16.2±0.2° 2-θ, 18.1±0.2° 2-θ, 19.0±0.2° 2-θ, 19.3±0.2° 2-θ, 19.6±0.2° 2-θ, 20.4±0.2° 2-θ, 20.7±0.2° 2-θ, 22.6±0.2° 2-θ, 22.9±0.2° 2-θ, 23.2±0.2° 2-θ, and 27.7±0.2° 2-θ, as measured by X-ray powder diffraction using an X-ray wavelength of 1.5406 Å. In some embodiments, the X-ray powder diffraction pattern comprises at least four peaks selected from 7.1±0.2° 2-θ, 9.8±0.2° 2-θ, 10.2±0.2° 2-θ, 11.6±0.2° 2-θ, 13.5±0.2° 2-θ, 14.4±0.2° 2-θ, 14.6±0.2° 2-θ, 14.8±0.2° 2-θ, 15.0±0.2° 2-θ, 16.2±0.2° 2-θ, 18.1±0.2° 2-θ, 19.0±0.2° 2-θ, 19.3±0.2° 2-θ, 19.6±0.2° 2-θ, 20.4±0.2° 2-θ, 20.7±0.2° 2-θ, 22.6±0.2° 2-θ, 22.9±0.2° 2-θ, 23.2±0.2° 2-θ, and 27.7±0.2° 2-θ, as measured by X-ray powder diffraction using an X-ray wavelength of 1.5406 Å. In some embodiments, the X-ray powder diffraction pattern comprises at least five peaks selected from 7.1±0.2° 2-θ, 9.8±0.2° 2-θ, 10.2±0.2° 2-θ, 11.6±0.2° 2-θ, 13.5±0.2° 2-θ, 14.4±0.2° 2-θ, 14.6±0.2° 2-θ, 14.8±0.2° 2-θ, 15.0±0.2° 2-θ, 16.2±0.2° 2-θ, 18.1±0.2° 2-θ, 19.0±0.2° 2 0, 19.3±0.2° 2-θ, 19.6±0.2° 2-θ, 20.4±0.2° 2-θ, 20.7±0.2° 2-θ, 22.6±0.2° 2-θ, 22.9±0.2°2-θ, 23.2±0.2° 2-θ, and 27.7±0.2° 2-θ, as measured by X-ray powder diffraction using an X-ray wavelength of 1.5406 Å. In some embodiments, the X-ray powder diffraction pattern comprises at least six peaks selected from 7.1±0.2° 2-θ, 9.8±0.2° 2-θ, 10.2±0.2° 2-θ, 11.6±0.2° 2-θ, 13.5±0.2° 2-θ, 14.4±0.2° 2-θ, 14.6±0.2° 2-θ, 14.8±0.2° 2-θ, 15.0±0.2° 2-θ, 16.2±0.2° 2-θ, 18.1±0.2° 2-θ, 19.0±0.2° 2-θ, 19.3±0.2° 2-θ, 19.6±0.2° 2-θ, 20.4±0.2° 2-θ, 20.7±0.2° 2-θ, 22.6±0.2° 2-θ, 22.9±0.2° 2-θ, 23.2±0.2° 2-θ, and 27.7±0.2° 2-θ, as measured by X-ray powder diffraction using an X-ray wavelength of 1.5406 Å. In some embodiments, the X-ray powder diffraction pattern comprises at least seven peaks selected from 7.1±0.2° 2-θ, 9.8±0.2° 2-θ, 10.2±0.2° 2-θ, 11.6±0.2° 2-θ, 13.5±0.2° 2-θ, 14.4±0.2° 2-θ, 14.6±0.2° 2-θ, 14.8±0.2° 2-θ, 15.0±0.2° 2-θ, 16.2±0.2° 2-θ, 18.1±0.2° 2-θ, 19.0±0.2° 2-θ, 19.3±0.2° 2-θ, 19.6±0.2° 2-θ, 20.4±0.2° 2-θ, 20.7±0.2° 2-θ, 22.6±0.2° 2-θ, 22.9±0.2° 2-θ, 23.2±0.2° 2-θ, and 27.7±0.2° 2-θ, as measured by X-ray powder diffraction using an X-ray wavelength of 1.5406 Å. In some embodiments, the X-ray powder diffraction pattern comprises at least eight peaks selected from 7.1±0.2° 2-θ, 9.8±0.2° 2-θ, 10.2±0.2° 2-θ, 11.6±0.2° 2-θ, 13.5±0.2° 2-θ, 14.4±0.2° 2-θ, 14.6±0.2° 2-θ, 14.8±0.2° 2-θ, 15.0±0.2° 2-θ, 16.2±0.2° 2-θ, 18.1±0.2° 2-θ, 19.0±0.2° 2-θ, 19.3±0.2° 2-θ, 19.6±0.2° 2-θ, 20.4±0.2° 2-θ, 20.7±0.2° 2-θ, 22.6±0.2° 2-θ, 22.9±0.2° 2-θ, 23.2±0.2° 2-θ, and 27.7±0.2° 2-θ, as measured by X-ray powder diffraction using an X-ray wavelength of 1.5406 Å. In some embodiments, the X-ray powder diffraction pattern comprises at least nine peaks selected from 7.1±0.2° 2-θ, 9.8±0.2° 2-θ, 10.2±0.2° 2-θ, 11.6±0.2° 2-θ, 13.5±0.2° 2-θ, 14.4±0.2° 2-θ, 14.6±0.2° 2-θ, 14.8±0.2° 2-θ, 15.0±0.2° 2-θ, 16.2±0.2° 2-θ, 18.1±0.2° 2-θ, 19.0±0.2° 2-θ, 19.3±0.2° 2-θ, 19.6±0.2° 2-θ, 20.4±0.2° 2-θ, 20.7±0.2° 2-θ, 22.6±0.2° 2-θ, 22.9±0.2° 2-θ, 23.2±0.2° 2-θ, and 27.7±0.2° 2-θ, as measured by X-ray powder diffraction using an X-ray wavelength of 1.5406 Å. In some embodiments, the X-ray powder diffraction pattern comprises at least ten peaks selected from 7.1±0.2° 2-θ, 9.8±0.2° 2-θ, 10.2±0.2° 2-θ, 11.6±0.2° 2-θ, 13.5±0.2° 2-θ, 14.4±0.2° 2-θ, 14.6±0.2° 2-θ, 14.8±0.2° 2-θ, 15.0±0.2° 2-θ, 16.2±0.2° 2-θ, 18.1±0.2° 2-θ, 19.0±0.2° 2-θ, 19.3±0.2° 2-θ, 19.6±0.2° 2-θ, 20.4±0.2° 2-θ, 20.7±0.2° 2-θ, 22.6±0.2° 2-θ, 22.9±0.2° 2-θ, 23.2±0.2° 2-θ, and 27.7±0.2° 2-θ, as measured by X-ray powder diffraction using an X-ray wavelength of 1.5406 Å. In some embodiments, the X-ray powder diffraction pattern comprises at least fifteen peaks selected from 7.1±0.2° 2-θ, 9.8±0.2° 2-θ, 10.2±0.2° 2-θ, 11.6±0.2° 2-θ, 13.5±0.2° 2-θ, 14.4±0.2° 2-θ, 14.6±0.2° 2-θ, 14.8±0.2° 2-θ, 15.0±0.2° 2-θ, 16.2±0.2° 2-θ, 18.1±0.2° 2-θ, 19.0±0.2° 2-θ, 19.3±0.2° 2-θ, 19.6±0.2° 2-θ, 20.4±0.2° 2-θ, 20.7±0.2° 2-θ, 22.6±0.2° 2-θ, 22.9±0.2° 2-θ, 23.2±0.2° 2-θ, and 27.7±0.2° 2-θ, as measured by X-ray powder diffraction using an X-ray wavelength of 1.5406 Å. In some embodiments, the X-ray powder diffraction pattern comprises peak at about 7.1° 2-θ, about 9.8°2-0, about 10.2° 2-θ, about 11.6° 2-θ, about 13.5° 2-θ, about 14.4° 2-θ, about 14.6° 2-θ, about 14.8° 2-θ, about 15.0° 2-θ, about 16.2° 2-θ, about 18.1° 2-θ, about 19.0° 2-θ, about 19.3° 2-θ, about 19.6° 2-θ, about 20.4° 2-θ, about 20.7° 2-θ, about 22.6° 2-θ, about 22.9° 2-θ, about 23.2° 2-θ, and about 27.7° 2-θ, as measured by X-ray powder diffraction using an X-ray wavelength of 1.5406 Å.

In some embodiments, Crystalline Form I is characterized by a differential scanning calorimetry (DSC) thermogram substantially the same as shown in FIG. 2.

In some embodiments, Crystalline Form I is characterized by a differential scanning calorimetry (DSC) thermogram comprising an endotherm in the range of about 80-90° C. In some embodiments, Crystalline Form I is characterized by a differential scanning calorimetry (DSC) thermogram comprising an endotherm with an onset of about 84° C. and a peak of about 86° C.

In some embodiments, Crystalline Form I is characterized by an endotherm at about 80-90° C., about 81-90° C., about 82-90° C., about 83-90° C., about 84-90° C., about 85-90° C., about 86-90° C., about 87-90° C., about 88-90° C., about 89-90° C., about 80-89° C., about 80-88° C., about 80-87° C., about 80-86° C., about 80-85° C., about 80-84° C., about 80-83° C., about 80-82° C., about 80-81° C., about 80-99° C., or about 80-99° C. in the DSC thermogram. In some embodiments, Crystalline Form I is characterized by an endotherm at about 80° C., 81° C., 82° C., 83° C., 84° C., 85° C., 86° C., 87° C., 88° C., 89° C., or 90° C. In some embodiments, the melting point of Crystalline Form I is about 87° C. In some embodiments, the melting point of Crystalline Form I is about 88° C. In some embodiments, the melting point of Crystalline Form I is 86-89° C.

In some embodiments, Crystalline Form I is characterized by a Thermogravimetric Analysis (TGA) thermogram substantially the same as shown in FIG. 3. In some embodiments, Crystalline Form I decomposes above a temperature of about 150° C. 200° C., about 250° C., about 300° C., about 350° C., about 400° C., about 450° C., about 500° C., about 550° C. or above 600° C. In some examples, Crystalline Form I decomposes above a temperature of about 250° C.

In some embodiments, Crystalline Form I is characterized by a Dynamic Vapor Sorption (DVS) trace substantially the same as shown in FIG. 4.

In some embodiments, Crystalline Form I is stable at room temperature. In some examples, Crystalline Form I can be stored at room temperature for extended period of time without significant chemical degradation or change in the crystalline form. In some examples, Crystalline Form I can be stored at room temperature for a time period of at least about 10 days, 30 days, 60 days, 90 days, 120 days, 150 days, or 180 days. In some examples, Crystalline Form I can be stored at room temperature for a time period of more than about 180 days. In some examples, Crystalline Form I can be stored at room temperature for a time period of 10-14 days, 10-18 days, 10-22 days, 10-26 days, 10-30 days, 10-40 days, 10-50 days, 10-60 days, 10-90 days, 10-120 days, 10-150 days, 10-180 days, 14-18 days, 14-22 days, 14-26 days, 14-30 days, 14-40 days, 14-50 days, 14-60 days, 14-90 days, 14-120 days, 14-150 days, 14-180 days, 18-22 days, 18-26 days, 18-30 days, 18-40 days, 18-50 days, 18-60 days, 18-90 days, 18-120 days, 18-150 days, 18-180 days, 22-26 days, 22-30 days, 22-40 days, 22-50 days, 22-60 days, 22-90 days, 22-120 days, 22-150 days, 22-180 days, 26-30 days, 26-40 days, 26-50 days, 26-60 days, 26-90 days, 26-120 days, 26-150 days, 26-180 days, 30-40 days, 30-50 days, 30-60 days, 30-90 days, 30-120 days, 30-150 days, 30-180 days, 40-50 days, 40-60 days, 40-90 days, 40-120 days, 40-150 days, 40-180 days, 50-60 days, 50-90 days, 50-120 days, 50-150 days, 50-180 days, 60-90 days, 60-120 days, 60-150 days, 60-180 days, 90-120 days, 90-150 days, or 90-180 days. In some examples, Crystalline Form I can be stored at room temperature for a time period of at least 10 days, 14 days, 18 days, 22 days, 26 days, 30 days, 40 days, 50 days, 60 days, 90 days, 120 days, 150 days, or 180 days.

Crystalline Form II of Compound 1

FIG. 5 shows the X-ray powder diffraction (XPRD) pattern for Crystalline Form II of Compound 1.

Figure 6:
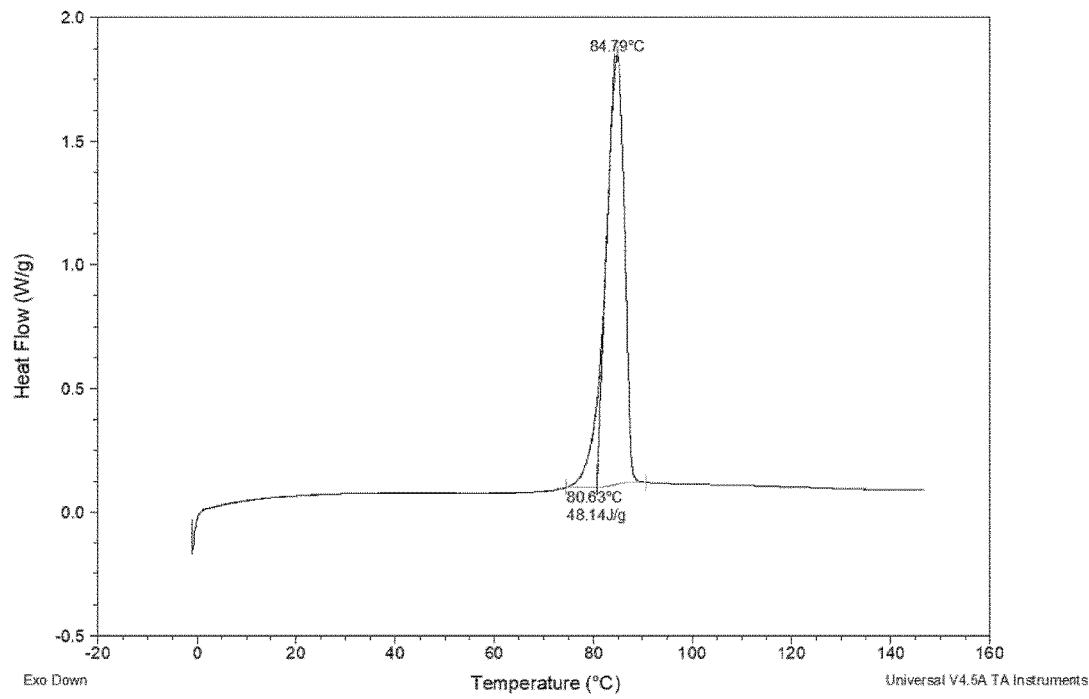
FIG. 6 shows the differential scanning calorimetry (DSC) thermogram for Crystalline Form II of Compound 1. The y-axis is labeled Heat Flow (W/g) from −0.5 to 2 at 0.5 unit intervals; the x-axis is labeled Temperature (degrees Celsius) from −20 to 160 at 20 unit intervals. The top of the peak is labeled 84.79 degrees Celsius, and the area at bottom of the peak is labeled 80.63 degrees Celsius 48.14 J/g.

FIG. 6 shows the differential scanning calorimetry (DSC) thermogram for Crystalline Form II of Compound 1.

Figure 7:
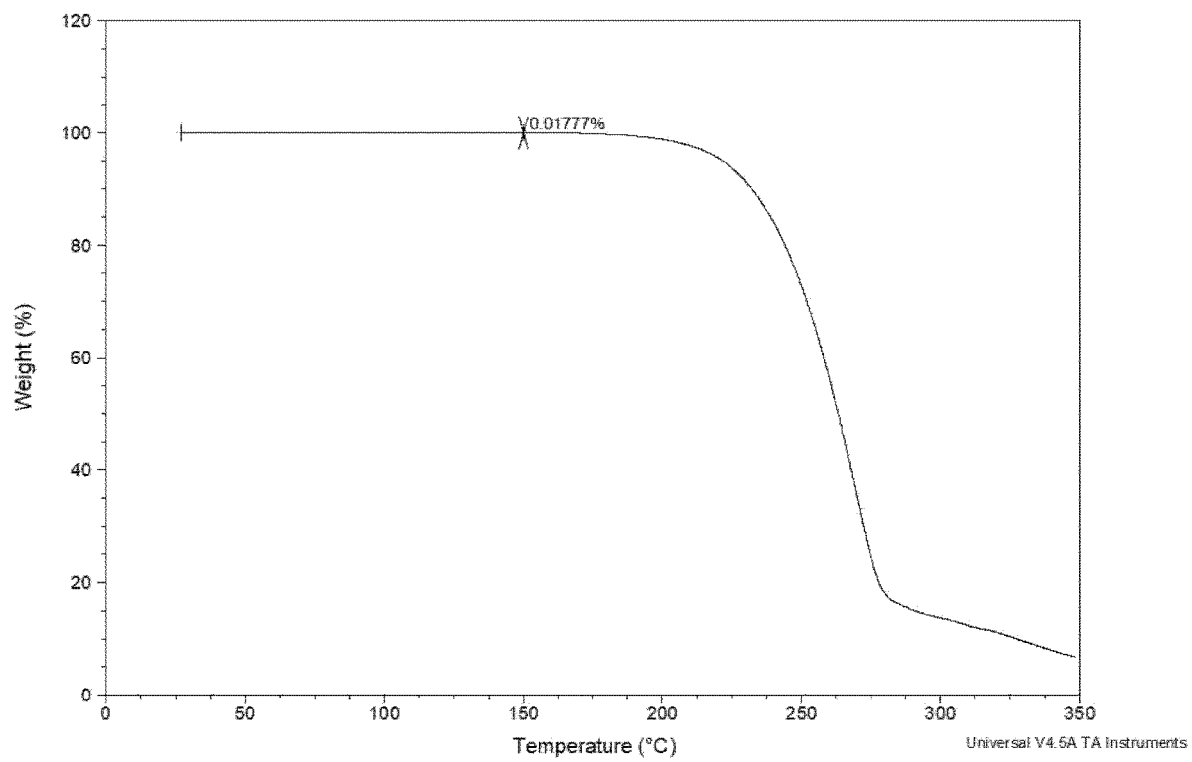
FIG. 7 shows the thermogravimetric analysis (TGA) thermogram for Crystalline Form II of Compound 1. The y-axis is labeled weight (%) from 0-120 at 20 unit intervals; the x-axis is labeled Temperature (degrees Celsius) from 0-350 at 50 unit intervals. Labeled with an X on the trace is 0.01777%.

FIG. 7 shows the thermogravimetric analysis thermogram for Crystalline Form II of Compound 1.

Figure 8:
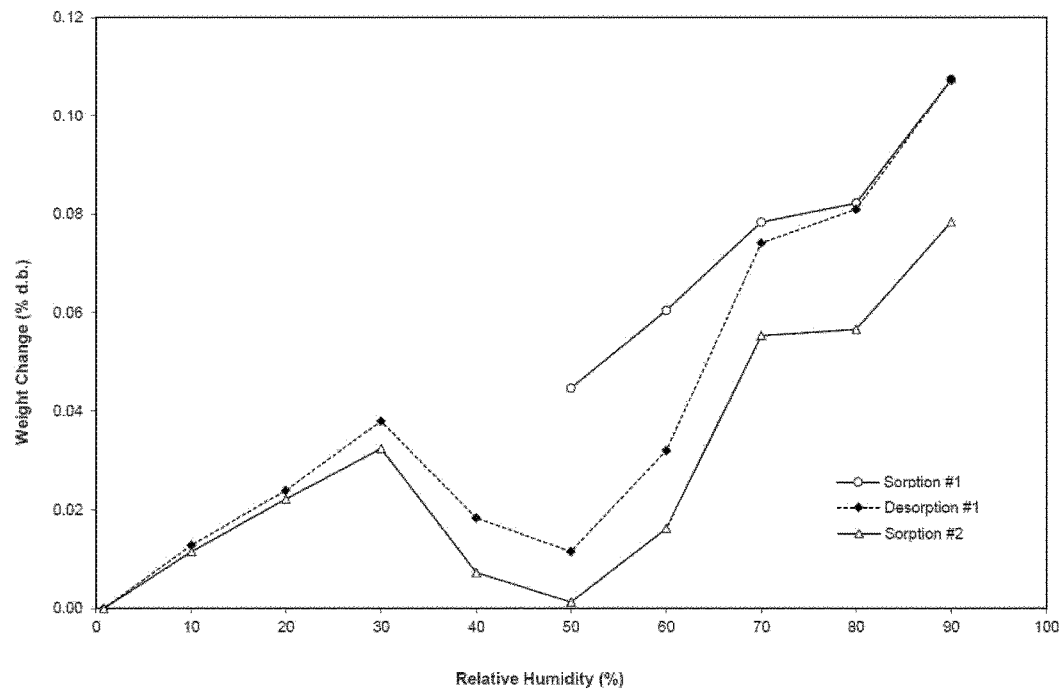
FIG. 8 shows the dynamic vapor sorption (DVS) trace for Crystalline Form II of Compound 1. The y-axis is labeled weight change (% d.b.) from 0.00 to 0.12 at 0.02 unit intervals; the x-axis is labeled relative humidity (%) from 0 to 100 at 10 unit intervals. The legend depicts Sorption #1 (solid line, open circles); Desorption #1 (dotted line, filled diamonds); and Sorption #2 (solid line, open triangles).

FIG. 8 shows the dynamic vapor sorption (DVS) trace for Crystalline Form II of Compound 1.

In some embodiments, the crystalline form of compound 1 is Crystalline Form II of (R)—N-(tert-butyl)-3-((4-chlorophenyl)(2-(trifluoromethyl)phenyl)methoxy)azetidine-1-carboxamide. In some embodiments, Crystalline Form II is characterized as having;

(a) an X-ray powder diffraction pattern comprising peaks at $15.2\pm0.2°$ 2-θ, $18.2\pm0.2°$2-θ, and $20.8\pm0.2°$ 2-θ as measured by X-ray powder diffraction using an X-ray wavelength of 1.5406 Å;
(b) an X-ray powder diffraction pattern substantially the same as shown in FIG. 5;
(c) a differential scanning calorimetry (DSC) thermogram comprising an endotherm in the range of about 80-90° C.;
(d) a differential scanning calorimetry (DSC) thermogram comprising an endotherm with an onset of about 81° C. and a peak of about 85° C.;
(e) a differential scanning calorimetry (DSC) thermogram substantially the same as shown in FIG. 6;
(f) a thermogravimetric analysis (TGA) thermogram substantially the same as shown in FIG. 7;
(g) a dynamic vapor sorption (DVS) trace substantially the same as shown in FIG. 8;
(h) an unchanged XPRD after storage at 25° C. and 90% relative humidity (RH);
(i) an unchanged XPRD after storage at laboratory conditions for at least 5 weeks;
or
(j) combinations thereof.

In some embodiments, the crystalline form of compound 1 is Crystalline Form II of (R)—N-(tert-butyl)-3-((4-chlorophenyl)(2-(trifluoromethyl)phenyl)methoxy)azetidine-1-carboxamide. In some embodiments, Crystalline Form II is characterized as having;

(a) an X-ray powder diffraction pattern comprising peaks at $15.2\pm0.2°$ 2-θ, $18.2\pm0.2°$2-θ, and $20.8\pm0.2°$ 2-θ as measured by X-ray powder diffraction using an X-ray wavelength of 1.5406 Å;
(b) an X-ray powder diffraction pattern substantially the same as shown in FIG. 5;
(c) a differential scanning calorimetry (DSC) thermogram comprising an endotherm in the range of about 80-90° C.;
(d) a differential scanning calorimetry (DSC) thermogram comprising an endotherm with an onset of about 81° C. and a peak of about 85° C.;
(e) a differential scanning calorimetry (DSC) thermogram substantially the same as shown in FIG. 6;
(f) a thermogravimetric analysis (TGA) thermogram substantially the same as shown in FIG. 7;
(g) a dynamic vapor sorption (DVS) trace substantially the same as shown in FIG. 8;
(h) a substantially unchanged XPRD after storage at 25° C. and 90% relative humidity (RH);
(i) a substantially unchanged XPRD after storage at laboratory conditions for at least 5 weeks;
or
(j) combinations thereof.

In some embodiments, Crystalline Form II is characterized by an X-ray powder diffraction pattern substantially the same as shown in FIG. 5.

In some embodiments, Crystalline Form II is characterized by an X-ray powder diffraction pattern comprising peaks at $15.2\pm0.2°$ 2-θ, $18.2\pm0.2°$ 2-θ, and $20.8\pm0.2°$ 2-θ, as measured by X-ray powder diffraction using an X-ray wavelength of 1.5406 Å. In some embodiments, Crystalline Form II is characterized by an X-ray powder diffraction pattern comprising peaks at about 15.2° 2-θ, about 18.2° 2-θ, and about 20.8° 2-θ, as measured by X-ray powder diffraction using an X-ray wavelength of 1.5406 Å.

In some embodiments, Crystalline Form II is characterized by an X-ray powder diffraction pattern further comprising at least one peak selected from $10.2\pm0.2°$ 2-θ, $19.2\pm0.2°$2-θ, $20.6\pm0.2°$ 2-θ, and $22.8\pm0.2°$ 2-θ, as measured by X-ray powder diffraction using an X-ray wavelength of 1.5406 Å. In some embodiments, Crystalline Form II is characterized by an X-ray powder diffraction pattern comprising peaks at about 10.2° 2-θ, about 19.2° 2-θ, about 20.6° 2-θ, and about 22.8° 2-θ, as measured by X-ray powder diffraction using an X-ray wavelength of 1.5406 Å.

In some embodiments, Crystalline Form II is characterized by an X-ray powder diffraction pattern further comprising at least one peak selected from $7.0\pm0.2°$ 2-θ, $9.8\pm0.2°$ 2 0, $13.6\pm0.2°$ 2-θ, $14.6\pm0.2°$ 2-θ, $15.0\pm0.2°$ 2-θ, $16.1\pm0.2°$ 2-θ, $19.7\pm0.2°$ 2-θ, $20.3\pm0.2°$2-θ, $20.4\pm0.2°$ 2-θ, as measured by X-ray powder diffraction using an X-ray wavelength of 1.5406 Å. In some embodiments, Crystalline Form II is characterized by an X-ray powder diffraction pattern fur comprising at least one peak selected from about 7.0° 2-θ, about 9.8° 2-θ, about 13.6° 2-θ, about 14.6° 2-θ, about 15.0° 2-θ, about 16.1° 2-θ, about 19.7° 2-θ, about 20.3°2-θ, and about 20.4° 2-θ, as measured by X-ray powder diffraction using an X-ray wavelength of 1.5406 Å.

In some embodiments, Crystalline Form II is characterized by an X-ray powder diffraction pattern comprising a peak selected from $7.0\pm0.2°$ 2-θ, $9.8\pm0.2°$ 2-θ, $10.2\pm0.2°$ 2 0, $13.6\pm0.2°$ 2-θ, $14.6\pm0.2°$ 2-θ, $15.0\pm0.2°$ 2-θ, $15.2\pm0.2°$ 2-θ, $16.1\pm0.2°$ 2-θ, $18.2\pm0.2°$2-θ, $19.2\pm0.2°$ 2-θ, $19.7\pm0.2°$ 2-θ, $20.3\pm0.2°$ 2-θ, $20.4\pm0.2°$ 2-θ, $20.6\pm0.2°$ 2-θ, $20.8\pm0.2°$2-θ, and $22.8\pm0.2°$ 2-θ, as measured by X-ray powder diffraction using an X-ray wavelength of 1.5406 Å.

In some embodiments, Crystalline Form II is characterized by an X-ray powder diffraction pattern comprising at least one peak selected from 7.0±0.2° 2-θ, 9.8±0.2° 2-θ, 10.2±0.2° 2-θ, 13.6±0.2° 2-θ, 14.6±0.2° 2-θ, 15.0±0.2° 2-θ, 15.2±0.2° 2-θ, 16.1±0.2° 2-θ, 18.2±0.2° 2-θ, 19.2±0.2° 2-θ, 19.7±0.2° 2-θ, 20.3±0.2° 2-θ, 20.4±0.2° 2-θ, 20.6±0.2° 2-θ, 20.8±0.2° 2-θ, and 22.8±0.2° 2-θ, as measured by X-ray powder diffraction using an X-ray wavelength of 1.5406 Å. In some embodiments, Crystalline Form II is characterized by an X-ray powder diffraction pattern comprising at least two peaks selected from 7.0±0.2° 2-θ, 9.8±0.2°2-θ, 10.2±0.2° 2-θ, 13.6±0.2° 2-θ, 14.6±0.2° 2-θ, 15.0±0.2° 2-θ, 15.2±0.2° 2-θ, 16.1±0.2°2-θ, 18.2±0.2° 2-θ, 19.2±0.2° 2-θ, 19.7±0.2° 2-θ, 20.3±0.2° 2-θ, 20.4±0.2° 2-θ, 20.6±0.2°2-θ, 20.8±0.2° 2-θ, and 22.8±0.2° 2-θ, as measured by X-ray powder diffraction using an X-ray wavelength of 1.5406 Å. In some embodiments, Crystalline Form II is characterized by an X-ray powder diffraction pattern comprising at least three peaks selected from 7.0±0.2° 2-θ, 9.8±0.2° 2-θ, 10.2±0.2° 2-θ, 13.6±0.2° 2-θ, 14.6±0.2° 2-θ, 15.0±0.2° 2-θ, 15.2±0.2° 2-θ, 16.1±0.2° 2-θ, 18.2±0.2° 2-θ, 19.2±0.2° 2-θ, 19.7±0.2° 2-θ, 20.3±0.2° 2-θ, 20.4±0.2° 2-θ, 20.6±0.2° 2-θ, 20.8±0.2° 2-θ, and 22.8±0.2° 2-θ, as measured by X-ray powder diffraction using an X-ray wavelength of 1.5406 Å. In some embodiments, Crystalline Form II is characterized by an X-ray powder diffraction pattern comprising at least four peaks selected from 7.0±0.2° 2-θ, 9.8±0.2° 2-θ, 10.2±0.2° 2-θ, 13.6±0.2° 2-θ, 14.6±0.2° 2-θ, 15.0±0.2° 2-θ, 15.2±0.2° 2-θ, 16.1±0.2° 2-θ, 18.2±0.2° 2-θ, 19.2±0.2° 2-θ, 19.7±0.2° 2-θ, 20.3±0.2° 2-θ, 20.4±0.2° 2-θ, 20.6±0.2° 2-θ, 20.8±0.2° 2-θ, and 22.8±0.2° 2-θ, as measured by X-ray powder diffraction using an X-ray wavelength of 1.5406 Å. In some embodiments, Crystalline Form II is characterized by an X-ray powder diffraction pattern comprising at least five peaks selected from 7.0±0.2° 2-θ, 9.8±0.2° 2-θ, 10.2±0.2° 2-θ, 13.6±0.2° 2-θ, 14.6±0.2° 2-θ, 15.0±0.2° 2-θ, 15.2±0.2° 2-θ, 16.1±0.2° 2-θ, 18.2±0.2° 2-θ, 19.2±0.2° 2-θ, 19.7±0.2° 2-θ, 20.3±0.2° 2-θ, 20.4±0.2° 2-θ, 20.6±0.2° 2-θ, 20.8±0.2° 2-θ, and 22.8±0.2° 2-θ, as measured by X-ray powder diffraction using an X-ray wavelength of 1.5406 Å. In some embodiments, Crystalline Form II is characterized by an X-ray powder diffraction pattern comprising at least six peaks selected from 7.0±0.2° 2-θ, 9.8±0.2° 2-θ, 10.2±0.2° 2-θ, 13.6±0.2° 2-θ, 14.6±0.2° 2-θ, 15.0±0.2° 2-θ, 15.2±0.2° 2-θ, 16.1±0.2° 2-θ, 18.2±0.2° 2-θ, 19.2±0.2° 2-θ, 19.7±0.2° 2-θ, 20.3±0.2° 2-θ, 20.4±0.2° 2-θ, 20.6±0.2° 2-θ, 20.8±0.2° 2-θ, and 22.8±0.2° 2-θ, as measured by X-ray powder diffraction using an X-ray wavelength of 1.5406 Å. In some embodiments, Crystalline Form II is characterized by an X-ray powder diffraction pattern comprising at least seven peaks selected from 7.0±0.2° 2-θ, 9.8±0.2° 2-θ, 10.2±0.2° 2-θ, 13.6±0.2° 2-θ, 14.6±0.2° 2-θ, 15.0±0.2° 2-θ, 15.2±0.2° 2-θ, 16.1±0.2° 2-θ, 18.2±0.2° 2-θ, 19.2±0.2° 2-θ, 19.7±0.2° 2-θ, 20.3±0.2° 2-θ, 20.4±0.2° 2-θ, 20.6±0.2° 2-θ, 20.8±0.2° 2-θ, and 22.8±0.2° 2-θ, as measured by X-ray powder diffraction using an X-ray wavelength of 1.5406 Å. In some embodiments, Crystalline Form II is characterized by an X-ray powder diffraction pattern comprising at least eight peaks selected from 7.0±0.2° 2-θ, 9.8±0.2° 2-θ, 10.2±0.2° 2-θ, 13.6±0.2° 2-θ, 14.6±0.2° 2-θ, 15.0±0.2° 2-θ, 15.2±0.2° 2-θ, 16.1±0.2° 2-θ, 18.2±0.2° 2-θ, 19.2±0.2° 2-θ, 19.7±0.2° 2-θ, 20.3±0.2° 2-θ, 20.4±0.2° 2-θ, 20.6±0.2° 2-θ, 20.8±0.2° 2-θ, and 22.8±0.2° 2-θ, as measured by X-ray powder diffraction using an X-ray wavelength of 1.5406 Å. In some embodiments, Crystalline Form II is characterized by an X-ray powder diffraction pattern comprising at least nine peaks selected from 7.0±0.2° 2-θ, 9.8±0.2° 2-θ, 10.2±0.2° 2-θ, 13.6±0.2° 2-θ, 14.6±0.2° 2-θ, 15.0±0.2° 2-θ, 15.2±0.2° 2-θ, 16.1±0.2° 2-θ, 18.2±0.2° 2-θ, 19.2±0.2° 2-θ, 19.7±0.2° 2-θ, 20.3±0.2° 2-θ, 20.4±0.2° 2-θ, 20.6±0.2° 2-θ, 20.8±0.2° 2-θ, and 22.8±0.2° 2-θ, as measured by X-ray powder diffraction using an X-ray wavelength of 1.5406 Å. In some embodiments, Crystalline Form II is characterized by an X-ray powder diffraction pattern comprising at least ten peaks selected from 7.0±0.2° 2-θ, 9.8±0.2° 2-θ, 10.2±0.2° 2-θ, 13.6±0.2° 2-θ, 14.6±0.2° 2-θ, 15.0±0.2° 2-θ, 15.2±0.2° 2-θ, 16.1±0.2° 2-θ, 18.2±0.2° 2-θ, 19.2±0.2° 2-θ, 19.7±0.2° 2-θ, 20.3±0.2° 2-θ, 20.4±0.2° 2-θ, 20.6±0.2° 2-θ, 20.8±0.2° 2-θ, and 22.8±0.2° 2-θ, as measured by X-ray powder diffraction using an X-ray wavelength of 1.5406 Å. In some embodiments, Crystalline Form II is characterized by an X-ray powder diffraction pattern comprising at least fifteen peaks selected from 7.0±0.2° 2-θ, 9.8±0.2° 2-θ, 10.2±0.2° 2-θ, 13.6±0.2° 2-θ, 14.6±0.2° 2-θ, 15.0±0.2° 2-θ, 15.2±0.2° 2-θ, 16.1±0.2° 2-θ, 18.2±0.2° 2-θ, 19.2±0.2° 2-θ, 19.7±0.2° 2-θ, 20.3±0.2° 2-θ, 20.4±0.2° 2-θ, 20.6±0.2° 2-θ, 20.8±0.2° 2-θ, and 22.8±0.2° 2-θ, as measured by X-ray powder diffraction using an X-ray wavelength of 1.5406 Å.

In some embodiments, Crystalline Form II is characterized by a differential scanning calorimetry (DSC) thermogram substantially the same as shown in FIG. 6. In some embodiments, Crystalline Form II is characterized by a differential scanning calorimetry (DSC) thermogram comprising an endotherm in the range of about 80-90° C. In some embodiments, Crystalline Form II is characterized by a differential scanning calorimetry (DSC) thermogram comprising an endotherm with an onset of about 81° C. and a peak of about 85° C.

In some embodiments, Crystalline Form II is characterized by an endotherm at about 80-90° C., about 81-90° C., about 82-90° C., about 83-90° C., about 84-90° C., about 85-90° C., about 86-90° C., about 87-90° C., about 88-90° C., about 89-90° C., about 80-89° C., about 80-88° C., about 80-87° C., about 80-86° C., about 80-85° C., about 80-84° C., about 80-83° C., about 80-82° C., about 80-81° C., about 80-99° C., or about 80-99° C. in the DSC thermogram. In some embodiments, Crystalline Form I is characterized by an endotherm at about 80° C., 81° C., 82° C., 83° C., 84° C., 85° C., 86° C., 87° C., 88° C., 89° C., or 90° C. In some embodiments, the melting point of Crystalline Form II is about 84° C. In some embodiments, the melting point of Crystalline Form II is about 85° C. In some embodiments, the melting point of Crystalline Form II is 83-86° C.

In some embodiments, Crystalline Form II is characterized by a Thermogravimetric Analysis (TGA) thermogram substantially the same as shown in FIG. 7. In some embodiments, Crystalline Form I decomposes above a temperature of about 150° C., about 200° C., about 250° C., about 300° C., about 350° C., about 400° C., about 450° C., about 500° C., about 550° C. or above 600° C. In some embodiments, Crystalline Form II decomposes above a temperature of about 250° C. In some embodiments, Crystalline Form II decomposes above a temperature of about 280° C.

In some embodiments, Crystalline Form II is characterized by a Dynamic Vapor Sorption (DVS) trace substantially the same as shown in FIG. 8.

In some embodiments, Crystalline Form II is stable at room temperature. In some examples, Crystalline Form II can be stored at room temperature for extended period of time without significant chemical degradation or change in the crystalline form. In some examples, Crystalline Form II can be stored at room temperature for a time period of at least about 10 days, 30 days, 60 days, 90 days, 120 days, 150 days, or 180 days. In some examples, Crystalline Form II can be stored at room temperature for a time period of more than about 180 days. In some examples, Crystalline Form II can be stored at room temperature for a time period of 10-14 days, 10-18 days, 10-22 days, 10-26 days, 10-30 days, 10-40 days, 10-50 days, 10-60 days, 10-90 days, 10-120 days, 10-150 days, 10-180 days, 14-18 days, 14-22 days, 14-26 days, 14-30 days, 14-40 days, 14-50 days, 14-60 days, 14-90 days, 14-120 days, 14-150 days, 14-180 days, 18-22 days, 18-26 days, 18-30 days, 18-40 days, 18-50 days, 18-60 days, 18-90 days, 18-120 days, 18-150 days, 18-180 days, 22-26 days, 22-30 days, 22-40 days, 22-50 days, 22-60 days, 22-90 days, 22-120 days, 22-150 days, 22-180 days, 26-30 days, 26-40 days, 26-50 days, 26-60 days, 26-90 days, 26-120 days, 26-150 days, 26-180 days, 30-40 days, 30-50 days, 30-60 days, 30-90 days, 30-120 days, 30-150 days, 30-180 days, 40-50 days, 40-60 days, 40-90 days, 40-120 days, 40-150 days, 40-180 days, 50-60 days, 50-90 days, 50-120 days, 50-150 days, 50-180 days, 60-90 days, 60-120 days, 60-150 days, 60-180 days, 90-120 days, 90-150 days, or 90-180 days. In some examples, Crystalline Form II can be stored at room temperature for a time period of at least 10 days, 14 days, 18 days, 22 days, 26 days, 30 days, 40 days, 50 days, 60 days, 90 days, 120 days, 150 days, or 180 days.

Provided herein are crystalline forms of (R)—N-(tert-butyl)-3-((4-chlorophenyl)(2-(trifluoromethyl)phenyl)methoxy)azetidine-1-carboxamide (Compound 1) that are stable at room temperature or about 20° C. In some instances, the crystalline form comprises Form I or Form II. In some instances, the compound is stable for at least 1, 2, 3, 6, 8, 10, 12, 16, 20, 24, 30, 36 or at least 48 months. In some instances, the compound is stable for at least 12 months. In some instances, the compound is stable for at least 12 months. In some instances, the compound is stable for at least 12 months under a relative humidity of at least 99%, 95%, 90%, 85%, 80%, 75%, 50%, 25%, or at least 10%. In some instances, the compound is stable for at least 12 months under a relative humidity of at least 90%. In some instances, the compound is stable for at least 12 months under a relative humidity of at least 50%. In some instances, the compound is stable for at least 24 months. In some instances, the compound is stable for at least 24 months under a relative humidity of at least 99%, 95%, 90%, 85%, 80%, 75%, 50%, 25%, or at least 10%. In some instances, the compound is stable for at least 24 months under a relative humidity of at least 90%. In some instances, the compound is stable for at least 24 months under a relative humidity of at least 50%. In some instances, the compound is stable for at least 6 months. In some instances, the compound is stable for at least 6 months. In some instances, the compound is stable for at least 6 months under a relative humidity of at least 99%, 95%, 90%, 85%, 80%, 75%, 50%, 25%, or at least 10%. In some instances, the compound is stable for at least 6 months under a relative humidity of at least 90%. In some instances, the compound is stable for at least 6 months under a relative humidity of at least 50%. In some instances, crystalline forms of (R)—N-(tert-butyl)-3-((4-chlorophenyl)(2-(trifluoromethyl)phenyl)methoxy)azetidine-1-carboxamide (Compound 1) are stable at 10-30° C. In some instances, crystalline forms of (R)—N-(tert-butyl)-3-((4-chlorophenyl)(2-(trifluoromethyl)phenyl)methoxy)azetidine-1-carboxamide (Compound 1) are stable at 4-30° C.

Compositions and Formulations

In another aspect, the present disclosure provides compositions, including pharmaceutical composition and injectable composition, comprising one or more crystalline forms of Compound 1, or a solvate or hydrate thereof.

In various embodiments, the ratio of desired crystalline form such as Crystalline Form I to all other crystalline forms in a composition is greater than about 1:1, 2:1, 3:1, 4:1, 5:1, 6:1, 7:1, 8:1, 9:1, or more w/w. In other embodiments, the ratio of Crystalline Form II to all other polymorphs is greater than about 1:1, 2:1, 3:1, 4:1, 5:1, 6:1, 7:1, 8:1, 9:1, or more w/w.

Pharmaceutical Composition

In one aspect, the present disclosure provides a pharmaceutical compositions comprising the crystalline (R)—N-(tert-butyl)-3-((4-chlorophenyl)(2-(trifluoromethyl)phenyl)methoxy)azetidine-1-carboxamide, and at least one pharmaceutically acceptable excipient. In some embodiments, the crystalline form of Compound 1 is Crystalline Form I. In some embodiments, the crystalline form of Compound 1 is Crystalline Form II.

In some embodiments, the one or more polymorphs of Compound 1 are formulated into pharmaceutical compositions. In specific embodiments, pharmaceutical compositions are formulated in a conventional manner using one or more physiologically acceptable carriers comprising excipients and auxiliaries which facilitate processing of the active compounds/polymorphs into preparations which can be used pharmaceutically. Proper formulation is dependent upon the route of administration chosen. Any pharmaceutically acceptable techniques, carriers, and excipients are used as suitable to formulate the pharmaceutical compositions described herein: *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pennsylvania 1975; Liberman, H. A. and Lachman, L., Eds., *Pharmaceutical Dosage Forms*, Marcel Decker, New York, N.Y., 1980; and *Pharmaceutical Dosage Forms* and Drug Delivery Systems, Seventh Ed. (Lippincott Williams & Wilkins 1999).

In some embodiments, the present disclosure provides pharmaceutical compositions comprising one or more polymorphs of Compound 1 and a pharmaceutically acceptable diluent(s), excipient(s), or carrier(s). In certain embodiments, the pharmaceutical compositions include one or more polymorphs of Compound 1.

A pharmaceutical composition, as used herein, refers to a mixture of one or more polymorphs of Compound 1 with other chemical components, such as carriers, stabilizers, diluents, dispersing agents, suspending agents, thickening agents, and/or excipients. In certain embodiments, the pharmaceutical composition facilitates administration of the polymorphs to an organism. In some embodiments, in practicing the methods of treatment or use as described herein, therapeutically effective amounts of one or more polymorphs of Compound 1 are administered in a pharmaceutical composition to a subject having a condition or disorder to be treated. In specific embodiments, the subject is a human. In certain embodiments, therapeutically effective amounts vary depending on the severity of the condition or disorder, the age and relative health of the subject and other factors. The one or more polymorphs of Compound 1 described herein are used singly or in combination with one or more therapeutic agents as components of mixtures.

In some embodiments, the polymorphs of Compound 1 are subjected to spray drying prior to being formulated.

In some embodiments, the pharmaceutical composition is formulated for oral, parenteral, intravenous (IV), intramuscular (IM), subcutaneous (SC), endotracheal, sublingual, buccal, intralingual, submental, transdermal, suppository, or intranasal administration.

In some embodiments, the pharmaceutical composition is formulated to deliver a therapeutically effective amount of the crystalline (R)—N-(tert-butyl)-3-((4-chlorophenyl)(2-(trifluoromethyl)phenyl)methoxy)azetidine-1-carboxamide in no more than 10 minutes. In some embodiments, the pharmaceutical composition is formulated to deliver a therapeutically effective amount of the crystalline (R)—N-(tert-butyl)-3-((4-chlorophenyl)(2-(trifluoromethyl)phenyl) methoxy)azetidine-1-carboxamide in no more than 5 minutes.

In one embodiment, the polymorphs described herein are formulated for oral administration. The polymorphs of Compound 1 are formulated by combining the polymorphs with, e.g., pharmaceutically acceptable carriers or excipients. In various embodiments, the polymorphs described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the polymorphs described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the polymorphs described herein is formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In one embodiment, one or more polymorphs of Compound 1 are formulated in an aqueous solution. In other embodiments, one or more polymorphs of Compound 1 are formulated for transmucosal administration. In still other embodiments wherein the one or more polymorphs described herein are formulated for other parenteral injections, appropriate formulations include aqueous or nonaqueous solutions. In specific embodiments, such solutions include physiologically compatible buffers and/or excipients.

In other embodiments, therapeutically effective amounts of at least one of the polymorphs of Compound 1 as described herein are formulated for buccal or sublingual administration. Formulations suitable for buccal or sublingual administration include, by way of example only, tablets, lozenges, or gels.

In still other embodiments, the polymorphs described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical composition of a polymorph of Compound 1 is formulated in a form suitable for parenteral injection as sterile suspension, solution or emulsion in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active polymorphs in water-soluble form. In additional embodiments, suspensions of the active polymorphs are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the polymorphs to allow for the preparation of highly concentrated solutions. Alternatively, in other embodiments, the active ingredient is in powder form for constitution with a suitable vehicle, e.g., sterile pyrogen-free water, before use.

In still other embodiments, the one or more polymorphs of Compound 1 are administered topically. The one or more polymorphs described herein are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the one or more polymorphs of Compound 1 are formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of the one or more polymorphs of Compound 1 is accomplished by means of iontophoretic patches and the like. In certain embodiments, transdermal patches provide controlled delivery of the one or more polymorphs of Compound 1. In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In other embodiments, the one or more polymorphs of Compound 1 are formulated for administration by inhalation. Various forms suitable for administration by inhalation include, but are not limited to, aerosols, mists or powders. Pharmaceutical compositions of the polymorphs of Compound 1 are conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatin for use in an inhaler or insufflator are formulated containing a powder mix of the compound and a suitable powder base such as lactose or starch.

In still other embodiments, the one or more polymorphs of Compound 1 are formulated in rectal compositions for suppository administration such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active polymorphs into preparations which can be used pharmaceutically. Proper formulation is dependent upon the route of administration chosen. Any pharmaceutically acceptable techniques, carriers, and excipients are optionally used as suitable. Pharmaceutical compositions comprising the one or more polymorphs of Compound 1 are manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one polymorph of Compound 1 described herein as an active ingredient. The active ingredient is in acid-free or base-free form, or in a pharmaceutically acceptable salt form. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions, comprising the one or more polymorphs of Compound 1 described herein include formulating the polymorphs with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutically acceptable carriers or excipients for formulations described herein may comprise one or more polymers. In some embodiments, the pharmaceutically acceptable carrier is a polymer. Examples of polymers suitable for oral, buccal, intranasal, transdermal, thin-film, suppository or other administration include biocompatible and biodegradable polymers. Further examples of biocompatible polymers include natural or synthetic polymers such as polystyrene, polylactic acid, polyketal, butadiene styrene, styreneacrylic-vinyl terpolymer, polymethylmethacrylate, polyethylmethacrylate, polyalkylcyanoacrylate, styrene-maleic anhydride copolymer, polyvinyl acetate, polyvinylpyridine, polydivinylbenzene, polybutyleneterephthalate, acrylonitrile, vinylchloride-acrylates, polycaprolactone, poly(alkyl cyanoacrylates), poly(lactic-co-glycolic acid), and the like. In some instances, the carrier is Labrasol. In some instances, the carrier is methyl cellulose. In further embodiments, the pharmaceutically acceptable carrier comprises one or more biodegradable polymers. Use of biodegradable polymers provides the advantages of using a formulation that will eventually disintegrate, which facilitates release of the benzofuran compound and elimination of the carrier in vivo. However, benzofuran compounds can also be released from the matrix of non-biodegradable polymers as a result of gradual efflux from channels within the polymer matrix, including those formed by soluble materials included in the polymer matrix.

Examples of biodegradable polymers include polylactide polymers include poly(D,L-lactide)s; poly(lactide-co-glycolide) (PLGA) copolymers; polyglycolide (PGA) and polydioxanone; caprolactone polymers; chitosan; hydroxybutyric acids; polyanhydrides and polyesters; polyphosphazenes; and polyphosphoesters. In some instances, the biodegradable polymer for use in the nanoparticles is poly-(D,L-lactide-co-glycolide).

Functionalized poly (D,L-lactide)s can also be used as biodegradable polymers in the nanoparticles described herein. Examples of functionalized poly(D,L-lactide)s include poly(L-lactide), acrylate terminated; poly(L-lactide), amine terminated; poly(L-lactide), azide terminated; poly(L-lactide), 2-bromoisobutyryl terminated; poly(L-lactide), 2-bromoisobutyryl terminated; poly(L-lactide) 4-cyano-4-[(dodecylsulfanylthiocarbonyl)sulfanyl]pentonate; poly(L-lactide)N-2-hydroxyethylmaleimide terminated; poly(L-lactide) 2-hydroxyethyl, methacrylate terminated; poly(L-lactide), propargyl terminated; or poly(L-lactide), thiol terminated.

Other biodegradable polymers that can be used in the nanoparticles include AB-35-eblock copolymers such as poly(ethylene glycol) methyl ether-block-poly(D,L-lactide); poly(ethylene glycol) methyl ether-block-poly(lactide-co-glycolide) PEG; poly(ethylene glycol)-block-poly(.epsilon.-caprolactone) methyl ether PEG; and polypyrrole-block-poly(caprolactone). Further biodegradable polymers include ABA triblock copolymers such as polylactide-block-poly(ethylene glycol)-block-polylactide PLA; poly(lactide-co-glycolide)-block-poly(ethylene glycol)-block-poly(lactide-co-glycolide); poly(lactide-co-caprolactone)-block-poly(ethylene glycol)-block-poly(lactide-co-caprolactone); polycaprolactone-block-polytetrahydrofuran-block-polycaprolactone; and polyglycolide-block-poly(ethylene glycol)-block-polyglycolide PEG.

Biodegradable polymers also include various natural polymers. Examples of natural polymers include polypeptides including those modified non-peptide components, such as saccharide chains and lipids; nucleotides; sugar-based biopolymers such as polysaccharides; cellulose; carbohydrates and starches; dextrans; lignins; polyamino acids; adhesion proteins; lipids and phospholipids (e.g., phosphorylcholine). In some embodiments, the polymer is a cellulose derivative such as hydroxypropyl methylcellulose polymers. Hydroxypropyl methyl cellulose (HPMC) is a non-ionic cellulose ether made through a series of chemical processes, with the natural polymer cellulose as the raw material. The product is a non-ionic cellulose ether in the shape of white powder, odorless and tasteless. HPMC is also known as hypromellose, is a methylcellulose modified with a small amount of propylene glycol ether groups attached to the anhydroglucose of the cellulose.

Useful pharmaceutical compositions also, optionally, include solubilizing agents to aid in the solubility of a polymorph of Compound 1. The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, useful pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, useful compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Still other useful compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Injectable Compositions

In some embodiments, the one or more polymorphs of Compound 1 as described herein are formulated into an injectable composition. In some embodiments, the injectable composition comprises one or more polymorphs of crystalline (R)—N-(tert-butyl)-3-((4-chlorophenyl)(2-(trifluoromethyl)phenyl)methoxy)azetidine-1-carboxamide, or the pharmaceutical composition described herein, an opioid antagonist, and a benzodiazepine antagonist. In some embodiments, the benzodiazepine antagonist is flumazenil. In some embodiments, the opioid antagonist is naloxone or naltrexone. In some embodiments, the opioid antagonist is samidorphan. In some embodiments, the opioid antagonist is naltrexone. In some embodiments, the injectable composition is formulated in a single dose injectable device.

Methods of Making Compound 1 and Polymorphic Forms Thereof

In another aspect, the present disclosure provides methods of making one or more polymorphs of Compound 1:

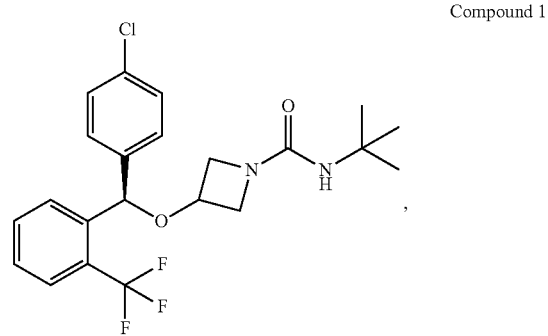 [SMILES: CC(C)(C)NC(=O)N1CC(O[C@H](c2ccc(Cl)cc2)c2ccccc2C(F)(F)F)C1]

Compound 1 or a pharmaceutically acceptable solvate or hydrate thereof.

The preparation and uses of Compound 1 have been previously described (see, Example 81 of U.S. Pat. No. 7,504,522, which is incorporated by reference).

In one aspect, the present disclosure is directed to methods of making polymorphs of Compound 1, or a pharmaceutically acceptable solvate or hydrate thereof, either by isolation of the desired polymorph as the first solid form after synthesis of Compound 1, or alternatively, by isolation of the desired polymorph as a transition from a prior solid form of Compound 1. Transitions from one form to another are within the scope of the present disclosure because they can be an alternative manufacturing method for obtaining the form desired for the production of the medicinal preparations.

Polymorphs of Compound 1, according to the methods of the present disclosure can be selected from Crystalline Form I, Crystalline Form II, and mixtures thereof.

Isolation and purification of the chemical entities and intermediates described herein can be performed, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples below. However, other equivalent separation or isolation procedures can also be used. Prior to crystallization, Compound 1 may be isolated in about 50% chemical purity, 55% chemical purity, 60% chemical purity, 65% chemical purity, 70% chemical purity, 75% chemical purity, 80% chemical purity, 90% chemical purity, 91% chemical purity, 92% purity, 93% chemical purity, 94% chemical purity, 95% chemical purity, 96% chemical purity, 97% chemical purity, 98% chemical purity, 99% chemical purity, about 98% chemical purity, or about 100% chemical purity.

In some embodiments, the crystalline forms disclosed herein are obtained by crystallizing Compound 1 with a chemical purity of less than about 98%, less than about 97%, less than about 96%, less than about 95%, less than about 94%, less than about 93%, less than about 92%, less than about 91%, less than about 90%, less than about 89%, less than about 88%, less than about 87%, less than about 86%, less than about 85%, less than about 84%, less than about 83%, less than about 82%, less than about 81%, less than about 80%, less than about 78%, less than about 76%, less than about 74%, less than about 72%, or less than about 70%. In some embodiments, the crystalline forms are obtained by crystallizing Compound 1 with a chemical purity in the range of about 70% to about 99%, 80% to about 96%, about 85% to about 96%, about 90% to about 96%, about 80% to 98%, about 85% to about 98%, about 90% to about 98%, about 92% to about 98%, about 94% to 98%, or about 96% to about 98%.

Preparation of Crystalline Form I

In one aspect, the present disclosure provides a method of preparing Crystalline Form I of (R)—N-(tert-butyl)-3-((4-chlorophenyl)(2-(trifluoromethyl)phenyl)methoxy)azetidine-1-carboxamide, wherein the method comprises:
  (a) dissolving the (R)—N-(tert-butyl)-3-((4-chlorophenyl)(2-(trifluoromethyl)phenyl)methoxy)azetidine-1-carboxamide in a solvent to obtain a solution; and
  (b) crystallizing the solution obtained in step (a) to obtain Crystalline Form I of (R)—N-(tert-butyl)-3-((4-chlorophenyl)(2-(trifluoromethyl)phenyl)methoxy)azetidine-1-carboxamide.

In some embodiments, the solvent in step (a) comprises water, heptane, methanol, acetone, or a combination thereof. In some embodiments, the solvent in step (a) is heptane. In some embodiments, the solvent in step (a) is mixture of acetone and water.

In some embodiments, the concentration of the solution obtained in step (a) is 20 mg/mL to 300 mg/mL. In some embodiments, the concentration of the solution obtained in step (a) is 40 mg/mL to 250 mg/mL. In some embodiments, the concentration of the solution obtained in step (a) is 100 mg/mL to 200 mg/mL. In some embodiments, the concentration of the solution obtained in step (a) is 125 mg/mL to 175 mg/mL. In some embodiments, the concentration of the solution obtained in step (a) is 100 mg/mL to 175 mg/mL. In some embodiments, the concentration of the solution obtained in step (a) is 50 mg/mL to 175 mg/mL. In some embodiments, the concentration of the solution obtained in step (a) is 75 mg/mL to 200 mg/mL. In some embodiments, the concentration of the solution obtained in step (a) is 20 mg/mL to 100 mg/mL. In some embodiments, the concentration of the solution obtained in step (a) is 20 mg/mL to 75 mg/mL. In some embodiments, the concentration of the solution obtained in step (a) is 200 mg/mL to 300 mg/mL.

In some embodiments, the desired polymorph is Crystalline Form I of Compound 1. In various embodiments, the desired polymorph is Crystalline Form I of Compound 1, and the isolating step involves recrystallization of Compound 1 from a binary, tertiary, or greater solvent system, collectively understood as a multi-solvent system. In some embodiments, the desired polymorph is Crystalline Form I of Compound 1, and the isolating step involves crystallization from a mono- or multi-solvent system, where the crystallization involves dissolving Compound 1 in the mono- or multi-solvent system at a temperature above ambient temperature. In some embodiments, the dissolving of Compound 1 in the mono- or multi-solvent system is performed at a temperature of about 0-90° C., 5-90° C., 10-90° C., 15-90° C., 20-90° C., 25-90° C., 30-90° C., 35-90° C., 40-90° C., 45-90° C., 50-90° C., 55-90° C., 60-90° C., 65-90° C., 70-90° C., 75-90° C., 80-90° C., 85-90° C., 0-80° C., 5-80° C., 10-80° C., 20-80° C., 30-80° C., 40-80° C., 50-80° C., 60-80° C., 70-80° C., 0-70° C., 5-70° C., 10-70° C., 15-70° C., 20-70° C., 30-70° C., 40-70° C., 50-70° C., 60-70° C., 0-60° C., 10-60° C., 20-60° C., 30-60° C., 40-60° C., or 50-60° C.

In various embodiments, the crystallization further involves actively heating the solution containing the dissolved Compound 1, for example to a temperature of about 40-100° C., 40-90° C., 40-80° C., 40-70° C., 40-60° C., 40-50° C., 50-100° C., 50-90° C., 50-80° C., 50-70° C., 50-60° C., 60-100° C., 60-90° C., 60-80° C., 60-70° C., 70-100° C., 70-90° C., 70-80° C., 80-100° C., or 80-90° C. In various embodiments, the solution containing the dissolved Compound 1 is maintained at the heated temperature for a period of time, for example for about 30 min, about 1 h, about 2 h, about 3 h, about 4 h, about 5 h, about 6 h, about 7 h, about 8 h, about 9 h, about 10 h, about 11 h, about 12 h, about 13 h, about 14 h, about 15 h, about 16 h, about 17 h, about 18 h, about 19 h, about 20 h, about 21 h, about 22 h, about 23 h, about 24 h or more.

In various embodiments, the crystallization further involves actively cooling the heated solution containing the dissolved Compound 1, for example to a temperature of about 0-40° C., 0-30° C., 0-20° C., 0-10° C., 10-40° C., 10-30° C., 10-20° C., 20-40° C., 20-30° C., 20-10° C., or 30° C. 40° C. In some embodiments, the crystallization further involves actively cooling the heated solution containing the dissolved Compound 1 to a temperature of about 20-30° C. In various embodiments, the solution containing the dissolved Compound 1 is further maintained at this lower temperature for a time period, for example for about 30 min, about 1 h, about 2 h, about 3 h, about 4 h, about 5 h, about 6 h, about 7 h, about 8 h, about 9 h, about 10 h, about 11 h, about 12 h, about 13 h, about 14 h, about 15 h, about 16 h, about 17 h, about 18 h, about 19 h, about 20 h, about 21 h, about 22 h, about 23 h, about 24 h or more.

In various embodiments, the steps of active heating followed by active cooling are repeated multiple times, for example at least 2, at least 3, at least 4, at least 5, at least 6, at least 7, at least 8, at least 9, or at least 10 times. In some embodiments, the steps of active heating followed by active cooling are repeated 2, 3, 4, 5, 6, 7, 8, 9, or 10 times.

In various embodiments, the crystallization further involves filtering the solution containing the obtained crystals of Compound 1. In some embodiments, the crystallization optionally involves washing the obtained crystals by a solvent, for example by the recrystallization solvent one or more times. In some embodiments, the crystallization optionally involves drying the obtained crystals, for example under vacuum.

In some embodiments, the chemical purity of Crystalline Form I is greater than 60%, 70%, 80%, 90%, 95%, or 99%. In some embodiments, the chemical purity of Crystalline Form I is greater than about 90%. In some embodiments, the chemical purity of Crystalline Form I is greater than about 95%. In some embodiments, the chemical purity of Crystalline Form I greater than about 99%. The chemical purity of Crystalline Form I may be measured by any available analytical technique, for example by HPLC analysis.

In various embodiments, Crystalline Form I is dry. In various embodiments, Crystalline Form I is non-solvated. In various embodiments, Crystalline Form I is non-hydrated. In various embodiments, Crystalline Form I is anhydrous.

Preparation of Crystalline Form II

In one aspect, the present disclosure provides a method of preparing Crystalline Form II of (R)—N-(tert-butyl)-3-((4-chlorophenyl)(2-(trifluoromethyl)phenyl)methoxy)azetidine-1-carboxamide, wherein the method comprises:
  (a) dissolving the (R)—N-(tert-butyl)-3-((4-chlorophenyl)(2-(trifluoromethyl)phenyl)methoxy)azetidine-1-carboxamide in a solvent to obtain a solution; and
  (b) crystallizing the solution obtained in step (a) to obtain Crystalline Form II of (R)—N-(tert-butyl)-3-((4-chlorophenyl)(2-(trifluoromethyl)phenyl)methoxy)azetidine-1-carboxamide.

In some embodiments, the solvent in step (a) comprises water, heptane, methanol, acetone, or a combination thereof. In some embodiments, the solvent in step (a) is heptane. In some embodiments, the solvent in step (a) is mixture of acetone and water.

In some embodiments, the concentration of the solution obtained in step (a) is 20 mg/mL to 300 mg/mL. In some embodiments, the concentration of the solution obtained in step (a) is 40 mg/mL to 250 mg/mL. In some embodiments, the concentration of the solution obtained in step (a) is 100 mg/mL to 200 mg/mL. In some embodiments, the concentration of the solution obtained in step (a) is 125 mg/mL to 175 mg/mL. In some embodiments, the concentration of the solution obtained in step (a) is 100 mg/mL to 175 mg/mL. In some embodiments, the concentration of the solution obtained in step (a) is 50 mg/mL to 175 mg/mL. In some embodiments, the concentration of the solution obtained in step (a) is 75 mg/mL to 200 mg/mL. In some embodiments, the concentration of the solution obtained in step (a) is 20 mg/mL to 100 mg/mL. In some embodiments, the concentration of the solution obtained in step (a) is 20 mg/mL to 75 mg/mL. In some embodiments, the concentration of the solution obtained in step (a) is 200 mg/mL to 300 mg/mL.

In some embodiments, the desired polymorph is Crystalline Form II of Compound 1. In various embodiments, the desired polymorph is Crystalline Form II of Compound 1, and the isolating step involves recrystallization of Compound 1 from a binary, tertiary, or greater solvent system, collectively understood as a multi-solvent system. In some embodiments, the desired polymorph is Crystalline Form II of Compound 1, and the isolating step involves crystallization from a mono- or multi-solvent system, where the crystallization involves dissolving Compound 1 in the mono- or multi-solvent system at a temperature above ambient temperature. In some embodiments, the dissolving of Compound 1 in the mono- or multi-solvent system is performed at a temperature of about 0-90° C., 5-90° C., 10-90° C., 15-90° C., 20-90° C., 25-90° C., 30-90° C., 35-90° C., 40-90° C., 45-90° C., 50-90° C., 55-90° C., 60-90° C., 65-90° C., 70-90° C., 75-90° C., 80-90° C., 85-90° C., 0-80° C., 5-80° C., 10-80° C., 20-80° C., 30-80° C., 40-80° C., 50-80° C., 60-80° C., 70-80° C., 0-70° C., 5-70° C., 10-70° C., 15-70° C., 20-70° C., 30-70° C., 40-70° C., 50-70° C., 60-70° C., 0-60° C., 10-60° C., 20-60° C., 30-60° C., 40-60° C., or 50-60° C.

In various embodiments, the crystallization further involves filtering the solution containing the obtained crystals of Compound 1. In some embodiments, the crystallization optionally involves washing the obtained crystals by a solvent, for example by the recrystallization solvent one or more times. In some embodiments, the crystallization optionally involves drying the obtained crystals, for example under vacuum.

In some embodiments, the chemical purity of Crystalline Form II is greater than 60%, 70%, 80%, 90%, 95%, or 99%. In some embodiments, the chemical purity of Crystalline Form II is greater than about 90%. In some embodiments, the chemical purity of Crystalline Form II is greater than about 95%. In some embodiments, the chemical purity of Crystalline Form II greater than about 99%. The chemical purity of Crystalline Form II may be measured by any available analytical technique, for example by HPLC analysis.

In various embodiments, Crystalline Form II is dry. In various embodiments, Crystalline Form II is non-solvated. In various embodiments, Crystalline Form II is non-hydrated. In various embodiments, Crystalline Form II is anhydrous.

Methods of Treatment

In one aspect, the present disclosure provides a method of treating known or suspected acute drug overdose reaction in a subject in need thereof, comprising administering to the subject a therapeutically effective amount of crystalline (R)—N-(tert-butyl)-3-((4-chlorophenyl)(2-(trifluoromethyl)phenyl)methoxy)azetidine-1-carboxamide, or the pharmaceutical composition as described herein.

In some embodiments, the subject shows signs of an acute cannabinoid overdose. In some embodiments, the acute cannabinoid overdose is caused by a compound from the *Cannabis* genus. In some embodiments, the acute cannabinoid overdose is caused by a synthetic cannabinoid. In some embodiments, the acute cannabinoid overdose is caused by oral ingestion of cannabinoids or synthetic cannabinoids. In some embodiments, the acute cannabinoid overdose is caused by oral ingestion of cannabinoids or synthetic cannabinoids. In some embodiments, the synthetic cannabinoid is capable of binding to the Cannabinoid (CB1) receptor. In some embodiments, the subject shows signs of cannabinoid hyperemesis syndrome.

In some embodiments, the method further comprising treatment for drug overdose prior to treatment with the crystalline (R)—N-(tert-butyl)-3-((4-chlorophenyl)(2-(trifluoromethyl)phenyl)methoxy)azetidine-1-carboxamide. In some embodiments, the prior treatment comprises one or more of administration of an opiate antagonist, activated charcoal, or emetic.

In another aspect, the present disclosure provides a method of using the crystalline (R)—N-(tert-butyl)-3-((4-chlorophenyl)(2-(trifluoromethyl)phenyl)methoxy)azetidine-1-carboxamide, or the pharmaceutical composition as described herein, comprising administering a therapeutically effective amount of the crystalline (R)—N-(tert-butyl)-3-((4-chlorophenyl)(2-(trifluoromethyl)phenyl)methoxy)azetidine-1-carboxamide prior to exposure to a cannabinoid. In some embodiments, the cannabinoid is tetrahydrocannabinol (THC).

In another aspect, the present disclosure provides a method of treating a subject suspected of a drug overdose, comprising administering a therapeutically effective amount of the crystalline (R)—N-(tert-butyl)-3-((4-chlorophenyl)(2-(trifluoromethyl)phenyl)methoxy)azetidine-1-carboxamide to the subject and monitoring said subject for reduced symptoms associated with overdose. In some embodiments, the monitoring comprises monitoring heart rate or respiration.

In another aspect, the present disclosure provides a method of treating cannabis use disorder (CUD) in a subject in need thereof, comprising administering a therapeutically effective amount of the crystalline (R)—N-(tert-butyl)-3-((4-chlorophenyl)(2-(trifluoromethyl)phenyl)methoxy)azetidine-1-carboxamide, or the pharmaceutical composition as described herein. In some embodiments, the subject is addicted to a compound from the *Cannabis* genus. In some embodiments, the subject is addicted to a synthetic cannabinoid. In some embodiments, the synthetic cannabinoid is capable of binding to the CB1 receptor.

In various embodiments of the methods as described herein, the crystalline (R)—N-(tert-butyl)-3-((4-chlorophenyl)(2-(trifluoromethyl)phenyl)methoxy)azetidine-1-carboxamide is Crystalline Form I. In another embodiment, the crystalline (R)—N-(tert-butyl)-3-((4-chlorophenyl)(2-(trifluoromethyl)phenyl)methoxy)azetidine-1-carboxamide is Crystalline Form II.

In various embodiments of the methods described herein, the method further comprising a diagnostic test prior to treatment with the crystalline (R)—N-(tert-butyl)-3-((4-chlorophenyl)(2-(trifluoromethyl)phenyl)methoxy)azetidine-1-carboxamide. In some embodiments, the diagnostic test is a blood test. In some embodiments, the subject has a cannabinoid plasma concentration of at least 25 µg/L. In some embodiments, the diagnostic test is a blood test. In some embodiments, the subject has a cannabinoid plasma concentration of at least 50 µg/L. In some embodiments, the subject has a cannabinoid plasma concentration of about 25 µg/L to 350 µg/L. In some embodiments, the subject has a cannabinoid plasma concentration of about 50 µg/L to 350 µg/L. In some embodiments, the subject has a cannabinoid plasma concentration of about 75 µg/L to 350 µg/L. In some embodiments, the subject has a cannabinoid plasma concentration of about 100 µg/L to 350 µg/L. In some embodiments, the subject has a cannabinoid plasma concentration of about 150 µg/L to 350 µg/L. In some embodiments, the subject has a cannabinoid plasma concentration of about 200 µg/L to 350 µg/L.

In various embodiments of the methods as described here, the amount of the crystalline (R)—N-(tert-butyl)-3-((4-chlorophenyl)(2-(trifluoromethyl)phenyl)methoxy)azetidine-1-carboxamide is between about 1 mg to about 200 mg. In another embodiment, the amount of the crystalline (R)—N-(tert-butyl)-3-((4-chlorophenyl)(2-(trifluoromethyl)phenyl)methoxy)azetidine-1-carboxamide is between about 5 mg to about 200 mg. In another embodiment, the amount of the crystalline (R)—N-(tert-butyl)-3-((4-chlorophenyl)(2-(trifluoromethyl)phenyl)methoxy)azetidine-1-carboxamide is between about 10 mg to about 200 mg. In another embodiment, the amount of the crystalline (R)—N-(tert-butyl)-3-((4-chlorophenyl)(2-(trifluoromethyl)phenyl)methoxy)azetidine-1-carboxamide is between about 15 mg to about 200 mg. In another embodiment, the amount of the crystalline (R)—N-(tert-butyl)-3-((4-chlorophenyl)(2-(trifluoromethyl)phenyl)methoxy)azetidine-1-carboxamide is between about 20 mg to about 200 mg. In another embodiment, the amount of the crystalline (R)—N-(tert-butyl)-3-((4-chlorophenyl)(2-(trifluoromethyl)phenyl)methoxy)azetidine-1-carboxamide is between about 25 mg to about 200 mg. In another embodiment, the amount of the crystalline (R)—N-(tert-butyl)-3-((4-chlorophenyl)(2-(trifluoromethyl)phenyl)methoxy)azetidine-1-carboxamide is between about 30 mg to about 200 mg. In another embodiment, the amount of the crystalline (R)—N-(tert-butyl)-3-((4-chlorophenyl)(2-(trifluoromethyl)phenyl)methoxy)azetidine-1-carboxamide is between about 35 mg to about 200 mg. In another embodiment, the amount of the crystalline (R)—N-(tert-butyl)-3-((4-chlorophenyl)(2-(trifluoromethyl)phenyl)methoxy)azetidine-1-carboxamide is between about 40 mg to about 200 mg. In another embodiment, the amount of the crystalline (R)—N-(tert-butyl)-3-((4-chlorophenyl)(2-(trifluoromethyl)phenyl)methoxy)azetidine-1-carboxamide is between about 45 mg to about 200 mg. In another embodiment, the amount of the crystalline (R)—N-(tert-butyl)-3-((4-chlorophenyl)(2-(trifluoromethyl)phenyl)methoxy)azetidine-1-carboxamide is between about 50 mg to about 200 mg. In another embodiment, the amount of the crystalline (R)—N-(tert-butyl)-3-((4-chlorophenyl)(2-(trifluoromethyl)phenyl)methoxy)azetidine-1-carboxamide is between about 75 mg to about 200 mg. In another embodiment, the amount of the crystalline (R)—N-(tert-butyl)-3-((4-chlorophenyl)(2-(trifluoromethyl)phenyl)methoxy)azetidine-1-carboxamide is between about 100 mg to about 200 mg. In another embodiment, the amount of the crystalline (R)—N-(tert-butyl)-3-((4-chlorophenyl)(2-(trifluoromethyl)phenyl)methoxy)azetidine-1-carboxamide is between about 125 mg to about 200 mg. In another embodiment, the amount of the crystalline (R)—N-(tert-butyl)-3-((4-chlorophenyl)(2-(trifluoromethyl)phenyl)methoxy)azetidine-1-carboxamide is between about 150 mg to about 200 mg. In another embodiment, the amount of the crystalline (R)—N-(tert-butyl)-3-((4-chlorophenyl)(2-(trifluoromethyl)phenyl)methoxy)azetidine-1-carboxamide is between about 175 mg to about 200 mg. In another embodiment, the amount of the crystalline (R)—N-(tert-butyl)-3-((4-chlorophenyl)(2-(trifluoromethyl)phenyl)methoxy)azetidine-1-carboxamide is 25-500, 25-400, 25-300, 25-250, 25-200, 25-150, 25-100, or 25-75 mg. In another embodiment, the amount of the crystalline (R)—N-(tert-butyl)-3-((4-chlorophenyl)(2-(trifluoromethyl)phenyl)methoxy)azetidine-1-carboxamide is 50-500, 50-400, 50-300, 50-250, 50-200, 50-150, 50-100, or 50-75 mg. In another embodiment, the amount of the crystalline (R)—N-(tert-butyl)-3-((4-chlorophenyl)(2-(trifluoromethyl)phenyl)methoxy)azetidine-1-carboxamide is 75-500, 75-400, 75-300, 75-250, 75-200, 75-150, 75-100, or 75-125 mg. In another embodiment, the amount of the crystalline (R)—N-(tert-butyl)-3-((4-chlorophenyl)(2-(trifluoromethyl)phenyl)methoxy)azetidine-1-carboxamide is 100-500, 100-400, 100-300, 100-250, 100-200, 100-150, 100-125 mg. In various embodiments of the methods as described here, the amount of (R)—N-(tert-butyl)-3-((4-chlorophenyl)(2-(trifluoromethyl)phenyl)methoxy)azetidine-1-carboxamide is between about 0.1 mg to about 200 mg. In another embodiment, the amount of (R)—N-(tert-butyl)-3-((4-chlorophenyl)(2-(trifluoromethyl)phenyl)methoxy)azetidine-1-carboxamide is between about 1 mg to about 200 mg. In another embodiment, the amount of (R)—N-(tert-butyl)-3-((4-chlorophenyl)(2-(trifluoromethyl)phenyl)methoxy)azetidine-1-carboxamide is between about 10 mg to about 50 mg. In another embodiment, the amount of (R)—N-(tert-butyl)-3-((4-chlorophenyl)(2-(trifluoromethyl)phenyl)methoxy)azetidine-1-carboxamide is between about 20 mg to about 30 mg. In another embodiment, the amount of (R)—N-(tert-butyl)-3-((4-chlorophenyl)(2-(trifluoromethyl)phenyl)methoxy)azetidine-1-carboxamide is between about 0.5 mg to about 200 mg. In another embodiment, the amount of (R)—N-(tert-butyl)-3-((4-chlorophenyl)(2-(trifluoromethyl)phenyl)methoxy)azetidine-1-carboxamide is between about 2 mg to about 200 mg. In another embodiment, the amount of (R)—N-(tert-butyl)-3-((4-chlorophenyl)(2-(trifluoromethyl)phenyl)methoxy)azetidine-1-carboxamide is between about 5 mg to about 200 mg. In another embodiment, the amount of (R)—N-(tert-butyl)-3-((4-chlorophenyl)(2-(trifluoromethyl)phenyl)methoxy)azetidine-1-carboxamide is between about 10 mg to about 200 mg. In another embodiment, the amount of (R)—N-(tert-butyl)-3-((4-chlorophenyl)(2-(trifluoromethyl)phenyl)methoxy)azetidine-1-carboxamide is between about 15 mg to about 200 mg. In another embodiment, the amount of (R)—N-(tert-butyl)-3-((4-chlorophenyl)(2-(trifluoromethyl)phenyl)methoxy)azetidine-1-carboxamide is between about 20 mg to about 200 mg. In another embodiment, the amount of (R)—N-(tert-butyl)-3-((4-chlorophenyl)(2-(trifluoromethyl)phenyl)methoxy)azetidine-1-carboxamide is between about 25 mg to about 200 mg. In another embodiment, the amount of (R)—N-(tert-butyl)-3-((4-chlorophenyl)(2-(trifluoromethyl)phenyl)methoxy)azetidine-1-carboxamide is between about 30 mg to about 200 mg. In another embodiment, the amount of (R)—N-(tert-butyl)-3-((4-chlorophenyl)(2-(trifluoromethyl)phenyl)methoxy)azetidine-1-carboxamide is between about 35 mg to about 200 mg. In another embodiment, the amount of (R)—N-(tert-butyl)-3-((4-chlorophenyl)(2-(trifluoromethyl)phenyl)methoxy)azetidine-1-carboxamide is between about 40 mg to about 200 mg. In another embodiment, the amount of (R)—N-(tert-butyl)-3-((4-chlorophenyl)(2-(trifluoromethyl)phenyl)methoxy)azetidine-1-carboxamide is between about 45 mg to about 200 mg. In another embodiment, the amount of (R)—N-(tert-butyl)-3-((4-chlorophenyl)(2-(trifluoromethyl)phenyl)methoxy)azetidine-1-carboxamide is between about 50 mg to about 200 mg. In another embodiment, the amount of (R)—N-(tert-butyl)-3-((4-chlorophenyl)(2-(trifluoromethyl)phenyl)methoxy)azetidine-1-carboxamide is between about 75 mg to about 200 mg. In another embodiment, the amount of (R)—N-(tert-butyl)-3-((4-chlorophenyl)(2-(trifluoromethyl)phenyl)methoxy)azetidine-1-carboxamide is between about 100 mg to about 200 mg. In another embodiment, the amount of (R)—N-(tert-butyl)-3-((4-chlorophenyl)(2-(trifluoromethyl)phenyl)methoxy)azetidine-1-carboxamide is between about 125 mg to about 200 mg. In another embodiment, the amount of (R)—N-(tert-butyl)-3-((4-chlorophenyl)(2-(trifluoromethyl)phenyl)methoxy)azetidine-1-carboxamide is between about 150 mg to about 200 mg. In another embodiment, the amount of (R)—N-(tert-butyl)-3-((4-chlorophenyl)(2-(trifluoromethyl)phenyl)methoxy)azetidine-1-carboxamide is between about 175 mg to about 200 mg. In another embodiment, the amount of (R)—N-(tert-butyl)-3-((4-chlorophenyl)(2-(trifluoromethyl)phenyl)methoxy)azetidine-1-carboxamide is 25-500, 25-400, 25-300, 25-250, 25-200, 25-150, 25-100, or 25-75 mg. In another embodiment, the amount of (R)—N-(tert-butyl)-3-((4-chlorophenyl)(2-(trifluoromethyl)phenyl)methoxy)azetidine-1-carboxamide is 50-500, 50-400, 50-300, 50-250, 50-200, 50-150, 50-100, or 50-75 mg. In another embodiment, the amount of (R)—N-(tert-butyl)-3-((4-chlorophenyl)(2-(trifluoromethyl)phenyl)methoxy)azetidine-1-carboxamide is 75-500, 75-400, 75-300, 75-250, 75-200, 75-150, 75-100, or 75-125 mg. In another embodiment, the amount of (R)—N-(tert-butyl)-3-((4-chlorophenyl)(2-(trifluoromethyl)phenyl)methoxy)azetidine-1-carboxamide is 100-500, 100-400, 100-300, 100-250, 100-200, 100-150, 100-125 mg. In another embodiment, the amount of (R)—N-(tert-butyl)-3-((4-chlorophenyl)(2-(trifluoromethyl)phenyl)methoxy)azetidine-1-carboxamide is 1-200 mg, 10-50 mg, 10-30 mg, or 20-30 mg. In another embodiment, the amount of (R)—N-(tert-butyl)-3-((4-chlorophenyl)(2-(trifluoromethyl)phenyl)methoxy)azetidine-1-carboxamide is 5-300 mg, 5-100 mg, or 10-30 mg. In another embodiment, the amount of (R)—N-(tert-butyl)-3-((4-chlorophenyl)(2-(trifluoromethyl)phenyl)methoxy)azetidine-1-carboxamide is 1-50, 1-30, 1-25, 1-20, 1-15, 1-20, 1-5, or 1-3 mg.

In various embodiments, the method is capable of ameliorating one or more symptoms of the acute drug overdose reaction in no more than 30 minutes. In another embodiment, the method is capable of ameliorating one or more symptoms of the acute drug overdose reaction in no more than 1 hour. In various embodiments, the method is capable of ameliorating one or more symptoms of the acute drug overdose reaction in no more than 10 minutes. In another embodiment, the method is capable of ameliorating one or more symptoms of the acute drug overdose reaction in no more than 15 minutes. In various embodiments, the method is capable of ameliorating one or more symptoms of the acute drug overdose reaction in no more than 45 minutes. In another embodiment, the method is capable of ameliorating one or more symptoms of the acute drug overdose reaction in no more than 20 minutes. In various embodiments, the method is capable of ameliorating one or more symptoms of the acute drug overdose reaction in 5-60, 5-45, 5-30, 5-25, 5-20, 5-15, 5-10, 10-60, 10-120, 10-30, 20-60, 20-120, 50-120, 60-120, or 90-120 minutes.

In various embodiments of the methods described herein, the amount of (R)—N-(tert-butyl)-3-((4-chlorophenyl)(2-(trifluoromethyl)phenyl)methoxy)azetidine-1-carboxamide in the bloodstream of the subject reaches at least 200 ng/mL within one hour after oral administration. In another embodiment, the amount of (R)—N-(tert-butyl)-3-((4-chlorophenyl)(2-(trifluoromethyl)phenyl)methoxy)azetidine-1-carboxamide in the bloodstream of the subject reaches at least 200 ng/mL within 50 minutes after oral administration. In another embodiment, the amount of (R)—N-(tert-butyl)-3-((4-chlorophenyl)(2-(trifluoromethyl)phenyl)methoxy)azetidine-1-carboxamide in the bloodstream of the subject reaches at least 200 ng/mL within 40 minutes after oral administration. In another embodiment, the amount of (R)—N-(tert-butyl)-3-((4-chlorophenyl)(2-(trifluoromethyl)phenyl)methoxy)azetidine-1-carboxamide in the bloodstream of the subject reaches at least 200 ng/mL within 30 minutes after oral administration. In another embodiment, the amount of (R)—N-(tert-butyl)-3-((4-chlorophenyl)(2-(trifluoromethyl)phenyl)methoxy)azetidine-1-carboxamide in the bloodstream of the subject reaches at least 200 ng/mL within 20 minutes after oral administration. In another embodiment, the amount of (R)—N-(tert-butyl)-3-((4-chlorophenyl)(2-(trifluoromethyl)phenyl)methoxy)azetidine-1-carboxamide in the bloodstream of the subject reaches at least 200 ng/mL within 10 minutes after oral administration. In another embodiment, the amount of (R)—N-(tert-butyl)-3-((4-chlorophenyl)(2-(trifluoromethyl)phenyl)methoxy)azetidine-1-carboxamide in the bloodstream of the subject reaches at least 200 ng/mL within 5 minutes after oral administration.

In various embodiments of the methods described herein, the amount of (R)—N-(tert-butyl)-3-((4-chlorophenyl)(2-(trifluoromethyl)phenyl)methoxy)azetidine-1-carboxamide in the bloodstream of the subject reaches at least 200 ng/mL within one hour after oral administration. In another embodiment, the amount of (R)—N-(tert-butyl)-3-((4-chlorophenyl)(2-(trifluoromethyl)phenyl)methoxy)azetidine-1-carboxamide in the bloodstream of the subject reaches at least 150 ng/mL within 50 minutes after oral administration. In another embodiment, the amount of (R)—N-(tert-butyl)-3-((4-chlorophenyl)(2-(trifluoromethyl)phenyl)methoxy)azetidine-1-carboxamide in the bloodstream of the subject reaches at least 150 ng/mL within 40 minutes after oral administration. In another embodiment, the amount of (R)—N-(tert-butyl)-3-((4-chlorophenyl)(2-(trifluoromethyl)phenyl)methoxy)azetidine-1-carboxamide in the bloodstream of the subject reaches at least 150 ng/mL within 30 minutes after oral administration. In another embodiment, the amount of (R)—N-(tert-butyl)-3-((4-chlorophenyl)(2-(trifluoromethyl)phenyl)methoxy)azetidine-1-carboxamide in the bloodstream of the subject reaches at least 150 ng/mL within 20 minutes after oral administration. In another embodiment, the amount of (R)—N-(tert-butyl)-3-((4-chlorophenyl)(2-(trifluoromethyl)phenyl)methoxy)azetidine-1-carboxamide in the bloodstream of the subject reaches at least 150 ng/mL within 10 minutes after oral administration. In another embodiment, the amount of (R)—N-(tert-butyl)-3-((4-chlorophenyl)(2-(trifluoromethyl)phenyl)methoxy)azetidine-1-carboxamide in the bloodstream of the subject reaches at least 150 ng/mL within 5 minutes after oral administration.

In some instances, (R)—N-(tert-butyl)-3-((4-chlorophenyl)(2-(trifluoromethyl)phenyl)methoxy)azetidine-1-carboxamide is dosed to provide a Tmax of no more than 5, 4, 3, 2.5, 2.25, 2, 1.75, 1.5, 1.25, 1, 0.75, 0.5, or 0.25 hours. In some instances, (R)—N-(tert-butyl)-3-((4-chlorophenyl)(2-(trifluoromethyl)phenyl)methoxy)azetidine-1-carboxamide is dosed to provide a Tmax of 0.1-5, 0.1-4, 0.1-3, 0.1-2, 0.1-1.5, 0.1-1, 0.25-3, 0.25-2, 0.25-1.5, 0.25-1, 0.5-3, 0.5-2.5, 0.5-2, 0.5-1.5, 0.5-1.25, 0.5-1, 0.5-0.75, or 0.75 hr. In some instances, (R)—N-(tert-butyl)-3-((4-chlorophenyl)(2-(trifluoromethyl)phenyl)methoxy)azetidine-1-carboxamide dosed at 100-200 mg provides a Tmax of 0.1-5, 0.1-4, 0.1-3, 0.1-2, 0.1-1.5, 0.1-1, 0.25-3, 0.25-2, 0.25-1.5, 0.25-1, 0.5-3, 0.5-2.5, 0.5-2, 0.5-1.5, 0.5-1.25, 0.5-1, 0.5-0.75, or 0.75 hr. In some instances, (R)—N-(tert-butyl)-3-((4-chlorophenyl)(2-(trifluoromethyl)phenyl)methoxy)azetidine-1-carboxamide dosed at 25-250 mg provides a Tmax of 0.1-5, 0.1-4, 0.1-3, 0.1-2, 0.1-1.5, 0.1-1, 0.25-3, 0.25-2, 0.25-1.5, 0.25-1, 0.5-3, 0.5-2.5, 0.5-2, 0.5-1.5, 0.5-1.25, 0.5-1, 0.5-0.75, or 0.75 hr. In some instances, (R)—N-(tert-butyl)-3-((4-chlorophenyl)(2-(trifluoromethyl)phenyl)methoxy)azetidine-1-carboxamide dosed at no more than 200 mg provides a Tmax of 0.1-5, 0.1-4, 0.1-3, 0.1-2, 0.1-1.5, 0.1-1, 0.25-3, 0.25-2, 0.25-1.5, 0.25-1, 0.5-3, 0.5-2.5, 0.5-2, 0.5-1.5, 0.5-1.25, 0.5-1, 0.5-0.75, or 0.75 hr. In some instances, (R)—N-(tert-butyl)-3-((4-chlorophenyl)(2-(trifluoromethyl)phenyl)methoxy)azetidine-1-carboxamide dosed at no more than 150 mg provides a Tmax of 0.1-5, 0.1-4, 0.1-3, 0.1-2, 0.1-1.5, 0.1-1, 0.25-3, 0.25-2, 0.25-1.5, 0.25-1, 0.5-3, 0.5-2.5, 0.5-2, 0.5-1.5, 0.5-1.25, 0.5-1, 0.5-0.75, or 0.75 hr. In some instances, (R)—N-(tert-butyl)-3-((4-chlorophenyl)(2-(trifluoromethyl)phenyl)methoxy)azetidine-1-carboxamide dosed at no more than 100 mg provides a Tmax of 0.1-5, 0.1-4, 0.1-3, 0.1-2, 0.1-1.5, 0.1-1, 0.25-3, 0.25-2, 0.25-1.5, 0.25-1, 0.5-3, 0.5-2.5, 0.5-2, 0.5-1.5, 0.5-1.25, 0.5-1, 0.5-0.75, or 0.75 hr. In some instances, (R)—N-(tert-butyl)-3-((4-chlorophenyl)(2-(trifluoromethyl)phenyl)methoxy)azetidine-1-carboxamide dosed at no more than 50 mg provides a Tmax of 0.1-5, 0.1-4, 0.1-3, 0.1-2, 0.1-1.5, 0.1-1, 0.25-3, 0.25-2, 0.25-1.5, 0.25-1, 0.5-3, 0.5-2.5, 0.5-2, 0.5-1.5, 0.5-1.25, 0.5-1, 0.5-0.75, or 0.75 hr. In some instances, (R)—N-(tert-butyl)-3-((4-chlorophenyl)(2-(trifluoromethyl)phenyl)methoxy)azetidine-1-carboxamide dosed at no more than 30 mg provides a Tmax of 0.1-5, 0.1-4, 0.1-3, 0.1-2, 0.1-1.5, 0.1-1, 0.25-3, 0.25-2, 0.25-1.5, 0.25-1, 0.5-3, 0.5-2.5, 0.5-2, 0.5-1.5, 0.5-1.25, 0.5-1, 0.5-0.75, or 0.75 hr. In some instances, (R)—N-(tert-butyl)-3-((4-chlorophenyl)(2-(trifluoromethyl)phenyl)methoxy)azetidine-1-carboxamide dosed at 10-50 mg provides a Tmax of 0.1-5, 0.1-4, 0.1-3, 0.1-2, 0.1-1.5, 0.1-1, 0.25-3, 0.25-2, 0.25-1.5, 0.25-1, 0.5-3, 0.5-2.5, 0.5-2, 0.5-1.5, 0.5-1.25, 0.5-1, 0.5-0.75, or 0.75 hr. In some instances, (R)—N-(tert-butyl)-3-((4-chlorophenyl)(2-(trifluoromethyl)phenyl)methoxy)azetidine-1-carboxamide dosed at 20-30 mg provides a Tmax of 0.1-5, 0.1-4, 0.1-3, 0.1-2, 0.1-1.5, 0.1-1, 0.25-3, 0.25-2, 0.25-1.5, 0.25-1, 0.5-3, 0.5-2.5, 0.5-2, 0.5-1.5, 0.5-1.25, 0.5-1, 0.5-0.75, or 0.75 hr.

In various embodiments, the method reduces the subject's ability to experience euphoria after inhaling or consuming *Cannabis* or a synthetic cannabinoid.

Compositions and formulations described herein may be administered as single or multiple doses. In some embodiments, described herein are methods of using the crystalline (R)—N-(tert-butyl)-3-((4-chlorophenyl)(2-(trifluoromethyl)phenyl)methoxy)azetidine-1-carboxamide as a single dose, one-time treatment for overdose THC or SC, or both. The overdose can also be from consumption of cannabis, synthetic cannabinoid, or any compound that is an agonist of the CB1 receptor. In some instances, methods described herein include treatment to children who inadvertently consume cannabis or cannabinoid edibles. In related aspects, any suspected overdose patient that presents a mentally disoriented or psychotic or cannot articulate the nature of their condition or the substances that have been ingested or administered can be treated with crystalline (R)—N-(tert-butyl)-3-((4-chlorophenyl)(2-(trifluoromethyl)phenyl)methoxy)azetidine-1-carboxamide.

In some embodiments, crystalline (R)—N-(tert-butyl)-3-((4-chlorophenyl)(2-(trifluoromethyl)phenyl)methoxy)azetidine-1-carboxamide prevent, treat, or reduce severity of various medical conditions and symptoms, including but not limited to, obesity, appetite disorder, another metabolic disorder, drug addiction and/or mental illness. In some instances, CB1 antagonists are used for the treatment of: addiction, alcoholism, Alzheimer's disease, anorexia nervosa, anxiety disorder, appetite disorders, attention deficit hyperactivity disorder, bipolar disorder, bulimia nervosa, cancer, cardiovascular disorders, central nervous system disease, cerebral ischemia, cerebral apoplexy, chemotherapy induced emesis, cocaine addiction, cognitive disorder, dementia, demyelination related disorders, diabetes, diabetic neuropathy, diarrhea, drug dependence, dystonia, eating disorder, emesis, epilepsy, female sexual dysfunction, functional bowel disorder, gastrointestinal disorders, gastric ulcers, generalized anxiety disorder, glaucoma, headache, Huntington's disease, impulse control disorders inflammation, irritable bowel syndrome, male sexual dysfunction, major depressive disorder, memory disorders menopause, migraine, muscle spasticity, multiple sclerosis, myalgia, nausea, neuralgia, neurodegenerative disorders, neuroinflammatory disorders, neuropathic pain, obsessive compulsive disorder, osteoarthritis, pain, panic disorder, Parkinson's disease, plaque sclerosis, premature ejaculation, premenstrual syndrome, psychosexual disorder, psychosis, rheumatoid arthritis, septic shock, schizophrenia, sexual disorders, sleep disorder, spinal cord injury, stroke, Tourette's syndrome, traumatic brain injury, tremor, urinary incontinence, and viral encephalitis.

The methods described herein include pre-exposure prophylaxis treatments. The long term effects of CB1 antagonism, which in some instances includes anhedonia, potentially makes them unsuitable for chronic use. However, in the same way that a subject who is addicted to alcohol might consume disulfiram before entering a situation when tempted to consume alcohol, one can take a CB1 antagonist, such as crystalline (R)—N-(tert-butyl)-3-((4-chlorophenyl)(2-(trifluoromethyl)phenyl)methoxy)azetidine-1-carboxamide, before encountering a situation where they may likely be exposed to or tempted to ingest THC or SCs or both. Similarly, in some instances, crystalline (R)—N-(tert-butyl)-3-((4-chlorophenyl)(2-(trifluoromethyl)phenyl)methoxy)azetidine-1-carboxamide is used to prevent effects from second hand smoke from marijuana. The method of using crystalline (R)—N-(tert-butyl)-3-((4-chlorophenyl)(2-(trifluoromethyl)phenyl)methoxy)azetidine-1-carboxamide in some instances includes use by a subject who wishes to gain acceptance to a situation or group by smoking marijuana or SCs, but also wants to remain mentally alert, such as during an undercover police or law enforcement investigation.

Additional Definitions

As used herein, "active agent" is used to indicate a chemical entity which has biological activity. In certain embodiments, an "active agent" is a compound having pharmaceutical utility. For example an active agent may be an anti-cancer therapeutic.

As used herein, "modulation" refers to a change in activity as a direct or indirect response to the presence of a chemical entity as described herein, relative to the activity of in the absence of the chemical entity. The change may be an increase in activity or a decrease in activity, and may be due to the direct interaction of the compound with the target or due to the interaction of the compound with one or more other factors that in turn affect the target's activity. For example, the presence of the chemical entity may, for example, increase or decrease the target activity by directly binding to the target, by causing (directly or indirectly) another factor to increase or decrease the target activity, or by (directly or indirectly) increasing or decreasing the amount of target present in the cell or organism.

As used herein, "therapeutically effective amount" of a chemical entity described herein refers to an amount effective, when administered to a human or non-human subject, to provide a therapeutic benefit such as amelioration of symptoms, slowing of disease progression, or prevention of disease.

"Treating" or "treatment" encompasses administration of Compound 1, or a pharmaceutically acceptable salt thereof, to a mammalian subject, particularly a human subject, in need of such an administration and includes (i) arresting the development of clinical symptoms of the disease, such as cancer, (ii) bringing about a regression in the clinical symptoms of the disease, such as cancer, and/or (iii) prophylactic treatment for preventing the onset of the disease, such as cancer.

As used herein, a "pharmaceutically acceptable" component is one that is suitable for use with humans and/or animals without undue adverse side effects (such as toxicity, irritation, and allergic response) commensurate with a reasonable benefit/risk ratio.

"Pharmaceutically acceptable salts" include, but are not limited to salts with inorganic acids, such as hydrochlorate, carbonate, phosphate, hydrogenphosphate, diphosphate, hydrobromate, sulfate, sulfinate, nitrate, and like salts; as well as salts with an organic acid, such as malate, malonate, maleate, fumarate, tartrate, succinate, citrate, acetate, lactate, gluconate, methanesulfonate, Tris (hydroxymethylaminomethane), p-toluenesulfonate, priopionate, 2-hydroxyethylsulfonate, benzoate, salicylate, stearate, oxalate, pamoate, and alkanoate such as acetate, HOOC—$(CH_2)_n$—COOH where n is 0-4, and like salts. Other salts include sulfate, methasulfonate, bromide, trifluoracetate, picrate, sorbate, benzilate, salicilate, nitrate, phthalate or morpholine. Pharmaceutically acceptable cations include, but are not limited to sodium, potassium, calcium, aluminum, lithium, and ammonium.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

As used herein, "subject" refers to a mammal that has been or will be the object of treatment, observation or experiment. The methods described herein can be useful in both human therapy and veterinary applications. In some embodiments, the subject is a human.

"Prodrugs" described herein include any compound that becomes Compound 1 when administered to a subject, e.g., upon metabolic processing of the prodrug. Similarly, "pharmaceutically acceptable salts" includes "prodrugs" of pharmaceutically acceptable salts. Examples of prodrugs include derivatives of functional groups, such as a carboxylic acid group, in Compound 1. Exemplary prodrugs of a carboxylic acid group include, but are not limited to, carboxylic acid esters such as alkyl esters, hydroxyalkyl esters, arylalkyl esters, and aryloxyalkyl esters. Other exemplary prodrugs include lower alkyl esters such as ethyl ester, acyloxyalkyl esters such as pivaloyloxymethyl (POM), glycosides, and ascorbic acid derivatives. Other exemplary prodrugs include amides of carboxylic acids. A discussion of prodrugs is provided in T. Higuchi and V. Stella, Pro-drugs as Novel Delivery Systems, Vol. 14 of the A.C.S. Symposium Series, in Edward B. Roche, ed., Bioreversible Carriers in Drug Design, American Pharmaceutical Association and Pergamon Press, 1987, and in Design of Prodrugs, ed. H. Bundgaard, Elsevier, 1985.

A "solvate" is formed by the interaction of a solvent and a compound. The term "compound" is intended to include solvates of compounds. Similarly, "pharmaceutically acceptable salts" includes solvates of pharmaceutically acceptable salts. Suitable solvates are pharmaceutically acceptable solvates, such as hydrates, including monohydrates and hemi-hydrates. Also included are solvates formed with the one or more crystallization solvents.

Pharmaceutically acceptable forms of the compounds recited herein include pharmaceutically acceptable salts, chelates, non-covalent complexes, prodrugs, and mixtures thereof.

A "chelate" is formed by the coordination of a compound to a metal ion at two (or more) points. The term "compound" is intended to include chelates of compounds. Similarly, "pharmaceutically acceptable salts" includes chelates of pharmaceutically acceptable salts.

A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding). Such non-covalent complexes are included in the term "compound". Similarly, pharmaceutically acceptable salts include "non-covalent complexes" of pharmaceutically acceptable salts.

When ranges are used herein for physical properties, such as molecular weight, or chemical properties, such as chemical formulae, all combinations and sub combinations of ranges and specific embodiments therein are intended to be included.

The term "about" when referring to a number or a numerical range means that the number or numerical range referred to is an approximation within experimental variability (or within statistical experimental error), and thus the number or numerical range may vary from, for example, between 1% and 15% of the stated number or numerical range. In some instances of numerical ranges, "about" means±10%.

As used herein, "significant" refers to any detectable change that is statistically significant in a standard parametric test of statistical significance such as Student's T-test, where $p<0.05$.

EXAMPLES

The following examples serve to further describe the manner of using the present disclosure. These examples are presented for illustrative purpose and should not serve to limit the true scope of the present disclosure.

In carrying out the procedures of the methods described herein, it is of course to be understood that references to particular buffers, media, reagents, cells, culture conditions, and the like are not intended to be limiting, but are to be read so as to include all related materials that one of ordinary skill in the art would recognize as being of interest or value in the particular context in which that discussion is presented. For example, it is often possible to substitute on buffer system or culture medium for another and still achieve similar, if not identical, results. Those of skill in the art will have sufficient knowledge of such systems and methodologies so as to able, without undue experimentation, to make such substitutions as will optimally serve their purposes in using the methods and procedures disclosed herein.

Example 1—Preparation and Characterization of Crystalline Form I of Compound 1

Preparation of Crystalline Form I

Crystalline Form I of (R)—N-(tert-butyl)-3-((4-chlorophenyl)(2-(trifluoromethyl)phenyl)methoxy)azetidine-1-carboxamide was suspended in heptane and stirred at room temperature. Partial dissolution was initially observed. After about 1 hour, change in appearance of the sample was noted with formation of a white precipitate. The slurry was then aged at room temperature for about 2 hours. The solid was then isolated by filtration and dried in vacuum at room temperature for about 1 hour.

X-Ray Powder Diffraction

A single crystal was irradiated with Cu-radiation at 160K using an X-ray wavelength of 1.5406 Å. The crystal diffracted to about 1.0 Å to 1.05 Å. The structure was solved in the chiral monoclinic space group I2 with a=19.371(2) A, b=9.7283(9) A, c=25.173(5) Å; β=111.07(1)°. The structure was successfully refined down to R1=7.64%, wR2=22.23%, GooF=1.04.

The XRPD pattern obtained from Crystalline Form I of compound 1 is summarized in Table 1 below and shown in FIG. 1.

TABLE 1

| XRPD Data of Crystalline Form I of Compound 1 | | |
| --- | --- | --- |
| Peak # | Angle (°2-θ) | Intensity (%) |
| 1 | 7.060 | 20.9 |
| 2 | 7.482 | 6.8 |
| 3 | 9.765 | 28.0 |
| 4 | 10.222 | 57.3 |
| 5 | 11.620 | 17.5 |
| 6 | 12.731 | 3.7 |
| 7 | 13.536 | 15.0 |
| 8 | 13.735 | 7.5 |
| 9 | 14.441 | 14.0 |
| 10 | 14.634 | 20.3 |
| 11 | 14.778 | 14.7 |
| 12 | 15.013 | 38.1 |
| 13 | 16.181 | 23.4 |
| 14 | 16.387 | 3.5 |
| 15 | 16.695 | 8.5 |
| 16 | 17.027 | 4.4 |
| 17 | 17.651 | 3.5 |
| 18 | 18.112 | 100.0 |
| 19 | 18.786 | 10.3 |
| 20 | 19.005 | 15.5 |
| 21 | 19.287 | 19.2 |
| 22 | 19.460 | 10.6 |
| 23 | 19.627 | 13.8 |
| 24 | 19.966 | 23.1 |
| 25 | 20.388 | 22.2 |
| 26 | 20.656 | 64.9 |
| 27 | 20.965 | 7.7 |
| 28 | 22.613 | 13.7 |
| 29 | 22.858 | 23.9 |
| 30 | 23.180 | 15.6 |
| 31 | 23.451 | 8.7 |
| 32 | 23.840 | 2.4 |
| 33 | 25.414 | 4.3 |
| 34 | 25.808 | 8.0 |
| 35 | 26.451 | 11.0 |
| 36 | 26.899 | 2.4 |
| 37 | 27.301 | 5.5 |
| 38 | 27.748 | 14.7 |
| 39 | 28.066 | 4.2 |
| 40 | 28.686 | 1.4 |
| 41 | 29.170 | 3.9 |
| 42 | 29.717 | 1.6 |

Differential Scanning Calorimetry (DSC)

The DSC trace of Crystalline Form I of (R)—N-(tert-butyl)-3-((4-chlorophenyl)(2-(trifluoromethyl)phenyl)methoxy)azetidine-1-carboxamide (compound 1) is reported in FIG. 2. It shows an endothermic event with onset at about 84° C. associated with melting.

Thermogravimetric Analysis (TGA)

The TGA trace of Crystalline Form I of (R)—N-(tert-butyl)-3-((4-chlorophenyl)(2-(trifluoromethyl)phenyl)methoxy)azetidine-1-carboxamide (compound 1) is reported in FIG. 3. It shows a weight loss of <0.1% up to 150° C.

Dynamic Vapor Sorption (DVS)

The DVS trace of Crystalline Form I of (R)—N-(tert-butyl)-3-((4-chlorophenyl)(2-(trifluoromethyl)phenyl)methoxy)azetidine-1-carboxamide (compound 1) is reported in FIG. 4. Crystalline Form I of compound 1 showed 0.4% weight gain from dryness to 90% RH during the second adsorption cycle.

Stability at Solid State

A sample of Crystalline Form I of (R)—N-(tert-butyl)-3-((4-chlorophenyl)(2-(trifluoromethyl)phenyl)methoxy)azetidine-1-carboxamide (compound 1) was re-analyzed by XRPD after 5 weeks of storage at laboratory conditions and did not show significant differences with respect to its initial XRPD pattern.

Example 2—Preparation and Characterization of Crystalline Form II of Compound 1 Preparation of Crystalline Form II Crystalline Form II of (R)—N-(tert-butyl)-3-((4-chlorophenyl)(2-(trifluoromethyl)phenyl)methoxy)azetidine-1-carboxamide (compound 1) was initially obtained from long term maturation of more than one week of Crystalline Form I of compound 1 in a solvent mixture of acetone and heptane. A scale-up re-preparation was performed starting from amorphous material of compound 1 for confirmation, as described below.

A sample of the amorphous material of compound 1 was suspended in a solvent mixture of acetone and heptane and stirred at room temperature. The initial gummy residue changed into a mobile slurry after about 10 days (XRPD of the solid showed Form I), followed by addition of a seed crystal of Crystalline Form II. The resulting mixture gradually changed into a thick suspension, and full conversion from Form I to Form II was detected after about 1 week. The solid was then isolated by filtration and dried overnight in vacuum over at room temperature.

X-Ray Powder Diffraction

A single crystal was irradiated with Cu-radiation at 160K using an X-ray wavelength of 1.5406 Å. The crystal diffracted to about 1.0 Å to 1.05 Å. The structure was solved in the chiral monoclinic space group I2 with a=19.371(2) Å, b=9.7283(9) Å, c=25.173(5) Å; β=111.07(1)°. The structure was successfully refined down to R1=7.64%, wR2=22.23%, GooF=1.04.

The XRPD pattern obtained from Crystalline Form I of compound 1 is summarized in Table 2 below and shown in FIG. 5.

TABLE 2

XRPD Data of Crystalline Form II of Compound 1

| Peak # | Angle (°2-θ) | Intensity (%) |
| --- | --- | --- |
| 1 | 7.047 | 27.7 |
| 2 | 7.567 | 9.6 |
| 3 | 9.814 | 31.5 |
| 4 | 10.243 | 65.2 |
| 5 | 11.730 | 25.3 |
| 6 | 12.782 | 8.2 |
| 7 | 13.554 | 29.1 |
| 8 | 13.773 | 17.1 |
| 9 | 14.102 | 1.9 |
| 10 | 14.570 | 28.9 |
| 11 | 14.973 | 36.9 |
| 12 | 15.162 | 82.1 |
| 13 | 16.085 | 34.4 |
| 14 | 16.491 | 4.3 |
| 15 | 16.899 | 24.1 |
| 16 | 18.156 | 100.0 |
| 17 | 18.565 | 8.4 |
| 18 | 18.838 | 13.5 |
| 19 | 19.223 | 50.3 |
| 20 | 19.483 | 13.5 |
| 21 | 19.691 | 29.2 |
| 22 | 20.276 | 32.6 |
| 23 | 20.407 | 31.7 |
| 24 | 20.568 | 59.1 |
| 25 | 20.780 | 77.9 |
| 26 | 21.079 | 13.3 |
| 27 | 21.464 | 7.5 |
| 28 | 22.789 | 50.6 |
| 29 | 23.033 | 9.4 |
| 30 | 23.510 | 22.3 |
| 31 | 23.676 | 8.9 |
| 32 | 24.159 | 17.8 |
| 33 | 25.652 | 19.0 |
| 34 | 26.554 | 15.0 |
| 35 | 27.154 | 5.0 |
| 36 | 27.290 | 6.7 |
| 37 | 27.564 | 5.5 |
| 38 | 27.782 | 8.9 |
| 39 | 28.402 | 6.0 |
| 40 | 28.717 | 4.2 |
| 41 | 29.325 | 10.7 |
| 42 | 29.795 | 7.4 |

Differential Scanning Calorimetry (DSC)

The DSC trace of Crystalline Form II of (R)—N-(tert-butyl)-3-((4-chlorophenyl)(2-(trifluoromethyl)phenyl)methoxy)azetidine-1-carboxamide (compound 1) is reported in FIG. 6. It shows an endothermic peak with onset at about 82° C. associated with melting.

Thermogravimetric Analysis (TGA)

The TGA trace of Crystalline Form II of (R)—N-(tert-butyl)-3-((4-chlorophenyl)(2-(trifluoromethyl)phenyl)methoxy)azetidine-1-carboxamide (compound 1) is reported in FIG. 7. It shows a weight loss of <0.1% up to 150° C.

Dynamic Vapor Sorption (DVS)

The DVS trace of Crystalline Form I of (R)—N-(tert-butyl)-3-((4-chlorophenyl)(2-(trifluoromethyl)phenyl)methoxy)azetidine-1-carboxamide (compound 1) is reported in FIG. 8. Crystalline Form II of compound 1 showed <0.1% weight gain from dryness to 90% RH during the second adsorption cycle. This indicated a non-hygroscopic behavior.

Stability at Solid State

A sample of Crystalline Form II of (R)—N-(tert-butyl)-3-((4-chlorophenyl)(2-(trifluoromethyl)phenyl)methoxy)azetidine-1-carboxamide (compound 1) was re-analyzed by XRPD after 8 weeks of storage at laboratory conditions and did not show significant differences with respect to its initial XRPD pattern.

Example 3—Investigation on the Relationship Between Crystalline Form I of Compound 1 and Crystalline Form II of Compound 1

The relationship between Crystalline Form I and Crystalline Form II of Compound 1 was investigated via competitive slurries and solubility determination.

Equimolar amounts of the Crystalline Form I and Crystalline Form II were suspended in saturated solution of compound 1 and aged in different conditions. Slurry samples were taken at intervals, solids were filtered, dried and analyzed by XRPD. Two temperatures, 20° C. and 40° C., and two different solvent systems, heptane and a mixture of ethanol and water, were investigated.

At 20° C., complete conversion to Crystalline Form II of Compound 1 was observed in both solvent systems. At 40° C., slow but complete conversion to Crystalline Form I of Compound 1 was observed.

The results of this study suggest that Crystalline Form II of Compound 1 is the most stable polymorph form at room temperature (20-21° C.).

Example 4—Solubility Studies of Crystalline Form I of Compound 1 and Crystalline Form II of Compound 1

Figure 9:
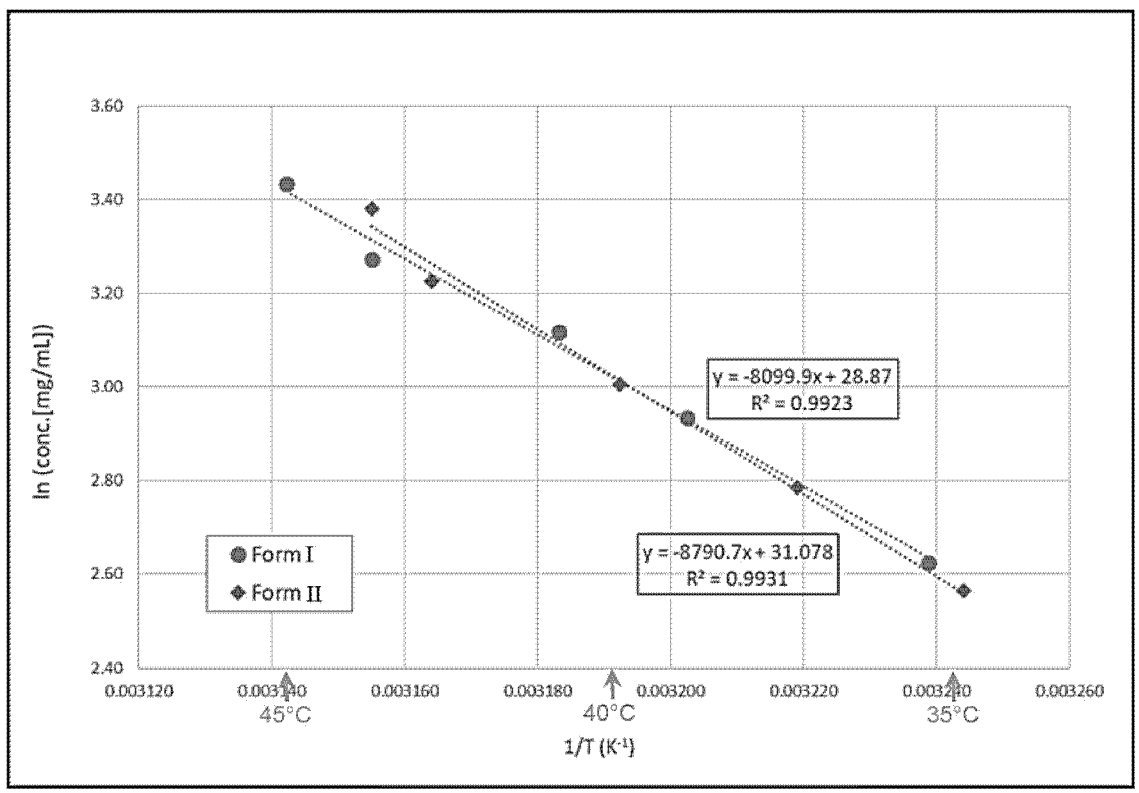
FIG. 9 shows the solubility vs. the reciprocal temperature (Arrhenius plots: ln[conc.] vs. 1/T [° K]) for Crystalline Form I of Compound 1 and Crystalline Form II of Compound 1. The y-axis is labeled ln (conc.[mg/mL]) from 2.40-3.60 at 0.20 unit intervals. The x-axis is labeled 1/T $(K^{-1})$ from 0.003120-0.003260 at 0.000020 unit intervals; temperatures 45, 40, and 35 degrees Celsius are labeled with arrows (left to right). The legend depicts Form I (filled circles) and Form II (filled diamonds). The line fit for Form I: $y=-8099.9x+28.87$, $R^2=0.9923$; Form II: $y=-8790.7x+31.078$, $R^2=0.9931$.

Temperature dependent solubility experiment was performed on Crystalline Form I and Crystalline Form II of Compound 1, and data was generated by Crystal16 equipment using heptane as solvent. Slurries with accurate amounts of solid in heptane were prepared, equilibrated at 20° C. for 5 minutes then heated to 70° C. at a rate of 5° C./min, and the turbidity of the suspensions were measured. Clear points of the solutions were determined and solubility vs. temperature curves (Arrhenius plots: ln[conc.] vs. 1/T [° K]) were obtained, as shown in FIG. 9.

Although small differences in solubility was observed, it was concluded that:

The two solubility lines intersect at about 39° C.;

The solubility of Crystalline Form II of Compound 1 is less than that of Crystalline Form I of Compound 1 at temperature less than 39° C.; and The solubility of Crystalline Form I of Compound 1 is less than that of Crystalline Form II of Compound 1 at temperature greater than 40° C.

The results and data from competitive slurries and temperature dependent solubility tests indicated an enantiotropic relationship between Crystalline Form I of Compound 1 and Crystalline Form II of Compound 1. It can be concluded that there is a transition temperature at 39-40° C., wherein Crystalline Form II of Compound 1 is more stable at temperatures less than 39° C., and Crystalline Form I of Compound 1 is more stable at temperatures greater than 40° C.

While some embodiments have been shown and described, various modifications and substitutions may be made thereto without departing from the spirit and scope of the present disclosure. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present disclosure has been described by way of illustration and not limitations on the scope of the claims.

The invention claimed is:

1. A method of preparing a crystalline form of (R)—N-(tert-butyl)-3-((4-chlorophenyl)(2-(trifluoromethyl)phenyl) methoxy)azetidine-1-carboxamide (Compound 1):

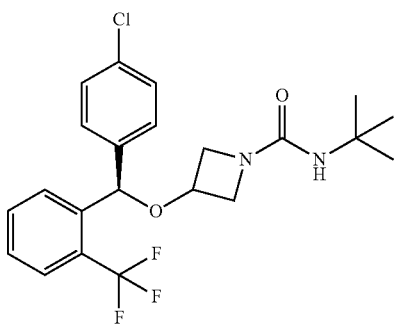 [SMILES: CC(C)(C)NC(=O)N1CC(O[C@H](c2ccc(Cl)cc2)c2ccccc2C(F)(F)F)C1]

Compound 1, wherein the method comprises: (a) dissolving the (R)—N-(tert-butyl)-3-((4-chlorophenyl)(2-(trifluoromethyl)phenyl)methoxy)azetidine-1-carboxamide in a solvent to obtain a solution; and (b) crystallizing the solution obtained in step (a).

2. The method of claim 1, wherein the (R)—N-(tert-butyl)-3-((4-chlorophenyl)(2-(trifluoromethyl)phenyl) methoxy)azetidine-1-carboxamide is amorphous in 3 step (a).

3. The method of claim 1, wherein the solvent in step (a) comprises water, heptane, methanol, acetone, or a combination thereof.

4. The method of claim 3, wherein the solvent in step (a) comprises heptane.

5. The method of claim 3, wherein the solvent in step (a) comprises a mixture of acetone and water.

6. The method of claim 1, wherein the concentration of the solution obtained in step (a) is 20 mg/mL to 300 mg/mL.

7. The method of claim 1, wherein the solution temperature is 10-40° C.

8. The method of claim 1, wherein the chemical purity of the crystalline form is greater than about 90%.

9. The method of claim 1, wherein the crystalline form is non-solvated.

10. The method of claim 1, wherein the crystalline form is anhydrous.

11. The method of claim 1, wherein the method further comprises mixing the crystalline form with one or more pharmaceutically acceptable excipients.

12. The method of claim 1, wherein the method further comprises formulating the crystalline form for oral administration.

13. The method of claim 12, wherein the method comprises formulating the crystalline form into a tablet, powder, pill, dragee, capsule, liquid, gel, syrup, elixir, slurry, or suspension.

14. The method of claim 13, wherein the tablet, powder, pill, dragee, capsule, liquid, gel, syrup, elixir, slurry, or suspension comprises 1-200 mg of (R)—N-(tert-butyl)-3-((4-chlorophenyl)(2-(trifluoromethyl)phenyl)methoxy)azetidine-1-carboxamide.

15. The method of claim 1, wherein the method further comprises formulating the crystalline form into a mixture for parenteral administration.

16. The method of claim 1, wherein the crystalline form comprises unit cell parameters at T=160° K of: a=19.371(2) Å, b=9.7283(9) Å, c=25.173(5) Å; β=111.07(1)° and a chiral monoclinic 12 space group.

17. A method of preparing a crystalline form of (R)—N-(tert-butyl)-3-((4-chlorophenyl)(2-(trifluoromethyl)phenyl) methoxy)azetidine-1-carboxamide (Compound 1):

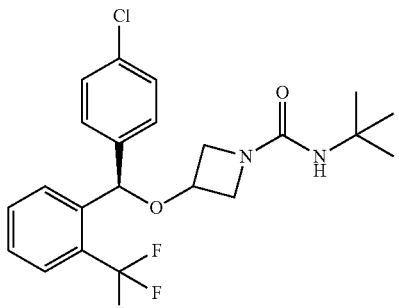

Compound 1, wherein the method comprises: (a) dissolving the (R)—N-(tert-butyl)-3-((4-chlorophenyl)(2-(trifluoromethyl)phenyl)methoxy)azetidine-1-carboxamide in a solvent to obtain a solution; and (b) crystallizing the solution obtained in step (a), wherein the crystalline (R)—N-(tert-butyl)-3-((4-chlorophenyl)(2-(trifluoromethyl)phenyl)methoxy)azetidine-1-carboxamide is characterized by:

(a) an X-ray powder diffraction pattern comprising peaks at 10.2±0.2° 2-θ, 18.1±0.2° 2-θ, and 20.7±0.2° 2-θ, as measured by X-ray powder diffraction using an X-ray wavelength of 1.5406 Å;

(b) an X-ray powder diffraction pattern substantially the same as shown in FIG. 1;

(c) a differential scanning calorimetry (DSC) thermogram comprising an endotherm in the range of about 80-90° C.;

(d) a differential scanning calorimetry (DSC) thermogram comprising an endotherm with an onset of about 84° C. and a peak of about 86° C.;
(e) a differential scanning calorimetry (DSC) thermogram substantially the same as shown in FIG. 2;
(f) a thermogravimetric analysis (TGA) thermogram substantially the same as shown in FIG. 3;
(g) a dynamic vapor sorption (DVS) trace substantially the same as shown in FIG. 4;
(h) a substantially unchanged XPRD after storage at 25° C. and 90% relative humidity (RH);
(i) a substantially unchanged XPRD after storage at laboratory conditions for at least 5 weeks; or
(j) combinations thereof.

18. A method of preparing a crystalline form of (R)—N-(tert-butyl)-3-((4-chlorophenyl)(2-(trifluoromethyl)phenyl)methoxy)azetidine-1-carboxamide (Compound 1):

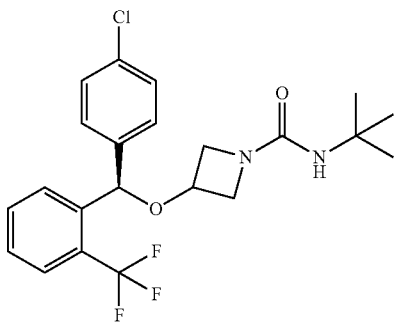 [SMILES: CC(C)(C)NC(=O)N1CC(O[C@H](c2ccc(Cl)cc2)c2ccccc2C(F)(F)F)C1]

Compound 1, wherein the method comprises: (a) dissolving the (R)—N-(tert-butyl)-3-((4-chlorophenyl)(2-(trifluoromethyl)phenyl)methoxy)azetidine-1-carboxamide in a solvent to obtain a solution; and (b) crystallizing the solution obtained in step (a),
wherein the crystalline (R)—N-(tert-butyl)-3-((4-chlorophenyl)(2-(trifluoromethyl)phenyl)methoxy)azetidine-1-carboxamide is characterized by:
(a) an X-ray powder diffraction pattern comprising peaks at 15.2±0.2° 2-θ, 18.2±0.2° 2-θ, and 20.8±0.2° 2-θ as measured by X-ray powder diffraction using an X-ray wavelength of 1.5406 Å;
(b) an X-ray powder diffraction pattern substantially the same as shown in FIG. 5;
(c) a differential scanning calorimetry (DSC) thermogram comprising an endotherm in the range of about 80-90° C.;
(d) a differential scanning calorimetry (DSC) thermogram comprising an endotherm with an onset of about 81° C. and a peak of about 85° C.;
(e) a differential scanning calorimetry (DSC) thermogram substantially the same as shown in FIG. 6;
(f) a thermogravimetric analysis (TGA) thermogram substantially the same as shown in FIG. 7;
(g) a dynamic vapor sorption (DVS) trace substantially the same as shown in FIG. 8;
(h) a substantially unchanged XPRD after storage at 25° C. and 90% relative humidity (RH);
(i) a substantially unchanged XPRD after storage at laboratory conditions for at least 5 weeks; or
(j) combinations thereof.

* * * * *